US012808866B2

(12) United States Patent
Kloppstech et al.

(10) Patent No.: US 12,808,866 B2
(45) **Date of Patent: *Nov. 24, 2026**

(54) DIGITAL SENSOR WITH REFERENCE CANTILEVER FOR CONVERTING CHEMICAL AND/OR BIOCHEMICAL INFORMATION

(71) Applicant: digid GmbH, Mainz (DE)

(72) Inventors: Konstantin Kloppstech, Mainz (DE); Constantin Von Gersdorff, Mainz (DE); Malte Bartenwerfer, Mainz (DE); Malte Koehler, Mainz (DE); Nils Koenne, Mainz (DE)

(73) Assignee: digid GmbH, Mainz (DE)

( * ) Notice: Subject to any disclaimer, the term of this patent is extended or adjusted under 35 U.S.C. 154(b) by 804 days.

This patent is subject to a terminal disclaimer.

(21) Appl. No.: 18/133,187

(22) Filed: Apr. 11, 2023

(65) Prior Publication Data

US 2023/0273201 A1 Aug. 31, 2023

Related U.S. Application Data

(63) Continuation of application No. PCT/EP2022/057647, filed on Mar. 23, 2022.

(30) Foreign Application Priority Data

Mar. 23, 2021 (DE) ......................... 102021107255.7

(51) Int. Cl.
*G01N 33/543* (2006.01)
*G01N 33/569* (2006.01)

(52) U.S. Cl.
CPC ... *G01N 33/5438* (2013.01); *G01N 33/56983* (2013.01)

(58) Field of Classification Search
None
See application file for complete search history.

(56) References Cited

U.S. PATENT DOCUMENTS 4,361,026 A * 11/1982 Muller ................. G01N 29/022
331/107 A
6,575,020 B1 6/2003 de Charmoy Grey et al.
(Continued)

FOREIGN PATENT DOCUMENTS

WO 2004029625 A2 4/2004
WO 2005116621 A1 12/2005
WO 2019002920 A1 1/2019

OTHER PUBLICATIONS

Arntz et al., "Label-free protein assay based on a nanomechanical cantilever array", Nanotechnology, vol. 14, No. 1, Dec. 2002, pp. 86-90.

*Primary Examiner* — Henry H Nguyen
(74) *Attorney, Agent, or Firm* — ArentFox Schiff LLP

(57) ABSTRACT

A sensor is provided for converting chemical and/or biochemical information about an analyte in a sample into an electrical signal. The sensor includes a test cantilever having a base and a deformable part of which a receptor layer is applied thereon for selective reception of an analyte of the sample. Moreover, on the base a passive test transducer is arranged and on the deformable part an active test transducer is arranged. The sensor further includes a reference cantilever having a base and a deformable part on which a reference layer is applied for selective non-reception of the analyte. Moreover, on the base a passive reference transducer is arranged and on the deformable part an active reference transducer is arranged.

20 Claims, 11 Drawing Sheets

(56) References Cited

U.S. PATENT DOCUMENTS

| | | | |
|---|---|---|---|
| 7,560,070 | B1 * | 7/2009 | Baller .............. G01N 33/54373 73/1.01 |
| 7,959,873 | B1 * | 6/2011 | Roukes ................. B81B 3/0021 422/402 |
| 2003/0010097 | A1 * | 1/2003 | Porter .................... B82Y 35/00 73/61.61 |
| 2003/0089182 | A1 | 5/2003 | Thaysen et al. |
| 2005/0034542 | A1 * | 2/2005 | Thaysen ............ G01N 33/5438 73/862.634 |
| 2006/0060003 | A1 * | 3/2006 | Thaysen .............. G01N 29/036 73/862.639 |
| 2006/0075803 | A1 * | 4/2006 | Boisen ................. G01N 29/036 73/866.5 |
| 2013/0133433 | A1 * | 5/2013 | Yoshikawa ............... G01L 1/18 73/774 |
| 2013/0283922 | A1 | 10/2013 | Qualtieri et al. |
| 2014/0352447 | A1 * | 12/2014 | Yoshikawa ............... G01L 1/18 73/774 |
| 2015/0316461 | A1 * | 11/2015 | Dunn ..................... G01N 15/05 73/61.65 |
| 2018/0195922 | A1 * | 7/2018 | Oono .................. G01L 19/0069 |
| 2019/0317081 | A1 | 10/2019 | Taslim et al. |
| 2020/0215537 | A1 | 7/2020 | Ndieyira |
| 2021/0293816 | A1 * | 9/2021 | Nawana ........... G01N 33/56983 |

* cited by examiner

DIGITAL SENSOR WITH REFERENCE CANTILEVER FOR CONVERTING CHEMICAL AND/OR BIOCHEMICAL INFORMATION

CROSS REFERENCE TO RELATED APPLICATIONS

This application is a continuation of PCT Application No. PCT/EP2022/057647, filed Mar. 23, 2022, which claims priority to German Patent Application No. 10 2021 107 255.7, filed Mar. 23, 2021, the entire contents of each of which are hereby incorporated by reference in their entirety.

TECHNICAL FIELD

The present invention relates to a sensor for converting chemical and/or biochemical information about an analyte in a sample into an electrical signal, in order thereby to derive a qualitative and/or quantitative statement regarding the presence of the analyte in the sample by means of the generated electrical signal.

BACKGROUND

Because of the worldwide increase in human infection rates with the Sars-CoV2 virus, one of the main pillars for stemming the epidemic is the extensive testing of patients and the timely tracing of infection chains.

To date there have been no reliable and cost-effective point-of-care screening tests available at the treatment location for the prompt diagnosis of a SARS-CoV-2 viral infection. The most widespread test is based on a reverse transcriptase PCR method (Corman V M, Landt O, Kaiser M, et al. Detection of 2019 novel coronavirus (2019-nCoV) by real-time RT-PCR. Euro Surveill. 2020; 25(3):2000045. doi: 10.2807/1560-7917.ES.2020.25.3.2000045) which entails a relatively high work effort as a result of the analysis in specialized diagnostic laboratories and an associated time outlay of up to three days between sampling and availability of the result for the medical staff and patient. This delay causes not only a relatively long-lasting uncertainty for the patient but also a significant delay both in the targeted treatment of the patient and in the application of appropriate measures for stemming the epidemic.

Existing point-of-care test methods are based on ascertaining the antiviral immune response via measurement of IgG and IgM antibodies (Li Z, Yi Y, Luo X, et al. Development and Clinical Application of A Rapid IgM-IgG Combined Antibody Test for SARS-CoV-2 Infection Diagnosis [published online ahead of print, 2020 Feb. 27]. J Med Virol. 2020; 10.1002/jmv.25727. doi:10.1002/jmv.25727) via lateral flow-based immunochromatographic methods. Virus-specific antibodies can be detected in the plasma, however, only 7 to 10 days after infection. In the case of SARS-CoV-2, though, patients are already highly infectious in the first week following infection. This represents one of the main reasons for the rapid worldwide spread of the COVID-19 pandemic.

WO 2007/088018 A1 proposes spring elements for use in biosensors such as in DNA analysis, for example.

The deformation of cantilevers by different surface stresses is described for example in Rasmussen, P. A., Hansen, O., & Boisen, A. (2005). Cantilever surface stress sensors with single-crystalline silicon piezoresistors. Applied Physics Letters, 86(20), 203502. https://doi.org/10.1063/1.1900299.

SUMMARY OF THE INVENTION

In view of the foregoing, it is an object of the present invention to provide an improved sensor for converting chemical and/or biochemical information.

According to an exemplary aspect, a sensor is provided for converting chemical and/or biochemical information about an analyte in a sample into an electrical signal. In this aspect, the sensor includes a test cantilever, which has a base and a deformable part, where at least on the deformable part a receptor layer for selective reception of an analyte of the sample is applied, where on the base a passive test transducer is arranged and on the deformable part an active test transducer is arranged, a reference cantilever, which has a base and a deformable part, where on the deformable part a reference layer for selective non-reception of the analyte is applied, where on the base a passive reference transducer is arranged and on the deformable part an active reference transducer is arranged, where the active and passive reference transducers and the active and passive test transducers are embodied and configured to output an electrical signal corresponding to the incidence and/or concentration of the analyte in the sample.

The base of the test cantilever and/or the base of the reference cantilever may be embodied as a rigid base. A rigid base here means that a deformation of the respective cantilever, i.e., of the test cantilever and/or of the reference cantilever, relative to the deformable part of the respective cantilever does not take place, or substantially does not take place. The rigid base here is, for example, connected to a substrate, supported by a substrate or machined out of the substrate. The deformable part of the test cantilever and/or of the reference cantilever, conversely, is not supported by the substrate, but is instead formed as protruding beyond an edge of the substrate and being accordingly free.

The deformable part of the test cantilever and/or of the reference cantilever may for example be deflectable. In that case the respective cantilever may be deflected around a bending edge formed in a transition region between the base and the deflectable region. The bending edge in this case is, for example, the edge of the substrate along which the cantilever is divided into the base and the deformable part.

The deformation of the respective cantilever in its deformable part is, however, not limited to a rising or falling deformation; the cantilever may also be deformed in itself, being for example bulged or corrugated or distorted.

A sample in this context refers to a limited amount of a substance that has been taken from a larger amount of the substance, for instance from a reservoir, where the composition of the sample is representative of the composition of the substance in the reservoir and accordingly the corresponding incidence in the reservoir may be derived from the incidence of substance and compositions of substance in the sample.

A sample may be, for example, a saliva sample, or a blood sample, or a swab, more particularly a throat swab or a nasal swab or a sinus swab, or tissue that has been removed. A sample in particular comprises any kind of biological sample, and also in particular samples from animals.

A sample may also be a nonbiological sample, such as a sample of a chemical substance, for example.

An analyte in this context is the substance whose presence in the sample is to be detected qualitative and/or quantitatively or is to be detected using the sensor. In particular, the analyte may be present directly in the sample, or may be in solution in the sample, or may adhere to the sample or a part of the sample, more particularly a sample particle. The analyte may also enter into a chemical, biological and/or physical interaction with the sample, allowing the analyte to be detected only indirectly via a corresponding interaction.

In particular, a form of sample may be converted into another form of sample, allowing the analyte, or its incidence, to be detected in a simple and reliable manner. For example, a swab may be dissolved in a fluid, so that the swab dissolved in the fluid is then the actual sample which is investigated for the analyte.

The analyte in the sample may also be chemically pretreated, for example—if the analyte is a virus—by opening the viral envelope in order to gain access to nucleocapsid antigens. Furthermore, the analyte may also be labeled by such pretreatment in order to boost the measurement signal. For this purpose, antibodies may bind to antigens in order to generate maximum deformation on the cantilever system.

The sample then contains the chemical information and/or biochemical information about the analyte. The chemical information may comprise, for example, the nature of the analyte, the concentration of the analyte, the incidence of the analyte, the weight of the analyte, the reactivity of the analyte, the density of the analyte, etc. The biochemical information comprises the same properties as the chemical information, but these substances may arise, for example, through biochemical processes. The information is said to be biochemical information in particular if the analyte has a particular influence on the biological cycle, for example the metabolism, or on the immune system.

The chemical and/or biochemical information is converted into an electrical signal. This may mean that an electrical signal can be altered or built up from the chemical composition of the analyte. This may concern, for example, the conductivity of a circuit. For example, first biochemical information may be present if the circuit is conductive, and second biochemical information may be present if the circuit is not conductive.

As well as the direct accessibility of the information, such as, for example, by the conductivity, it is also possible, however, to conclude the biochemical information through a physical and/or chemical process and/or an interaction.

For this purpose, the proposed sensor comprises a reference cantilever and a test cantilever. A cantilever in this context is a spring element which has a base and a deformable part. The base correspondingly is a stationary part of the cantilever, which is arranged in particular in a fixed location on a substrate. The base may be embodied, for example, as a rigid base. The deformable part of the cantilever is arranged on the base and protrudes beyond the substrate on which the base is arranged. In particular the base and the cantilever may formed as a single piece. In other words, the deformable part of the cantilever is suspended on the base on one side. Since the deformable part protrudes beyond the substrate, the deformable part of the cantilever is able to bend, deflect and stretch. The spatial limit beyond which the cantilever is bendable or the cantilever transitions from the base into the deformable part is called the bending edge. The bending edge is typically an edge of the substrate if the cantilever protrudes beyond the substrate.

If the cantilever is deformed, material stresses and forces result in or on the material of the cantilever, and can be measured. Where such material stress and/or force can be measured, a deformation of the cantilever can be derived.

The purpose of the transducers is to ascertain or measure the deformation or the alteration in the surface stress of the cantilevers. The active transducers are arranged on the deformable parts of the cantilevers, whereas the passive transducers are arranged on the bases, the rigid bases for example, of the cantilevers. In particular, electrical properties of a circuit may be influenced by way of the transducers.

For example, a deformation or an alteration in the surface stress of the cantilever may result in an increase in the resistance of a transducer, the active transducer for example, whereas no deformation or no alteration in the surface stress of the cantilever does not alter the resistance of the transducer. This may take place, for example, via the embodiment of the transducers according to the principle of a strain gauge, as a result of which a deformation of the respective cantilever is manifested in a change in length of the transducer strain gauge applied thereon, and hence a deformation of the cantilever may be detected directly by an alteration in the resistance of the strain gauge.

The chemical and/or biochemical information about the analyte is therefore detectable via a deformation of the cantilever, a subsequent registration via a transducer, and, finally, via a change in an electrical property of a circuit.

Located on the reference cantilever is a reference layer for selective non-reception of the analyte, whereas a receptor layer for reception of the analyte is applied on the test cantilever. A receptor layer here is a substance which is able to interact with the analyte. Interactions in this case means that the analyte is in chemical and/or biochemical and/or physical interaction with the receptor layer. This means in turn that that the receptor layer is chosen specifically for each analyte.

Overall, the reference layer is ideally very similar chemically to the receptor layer, but preferably does not bind to any of the chemical species present in the sample.

In other words, the surfaces of the test cantilever and of the reference cantilever are preferably identical chemically in respect of possible interfering influences, but the reference cantilever does not respond with binding to any of the chemical species incident in the sample. The behavior of the reference cantilever is therefore preferably nondynamic and it does not bind to anything in the sample.

For example, a first analyte interacts only with a first receptor layer, while another analyte interacts only with another receptor layer. In contrast to this, the reference layer is a substance with which the analyte explicitly does not interact. This means in turn that the reference layer as well is analyte-specific and must be selected accordingly.

A common feature of the reference layer and the receptor layer advantageously is that the interaction with substances which are not the analyte is equally strong or equally weak for both layers. Accordingly, a substance which is not the analyte interacts just as strongly or just as weakly with the receptor layer as with the reference layer.

The selective reception of the analyte on the test cantilever has the effect that the test cantilever responds sensitively to the analyte with a deformation and/or change in surface stress, and a signal is thereby generated by the transducers. Correspondingly, the other substances in the sample that are not the analyte contribute merely to a background noise on the test cantilever.

In other words, as a result of the selective non-reception of the analyte at the reference layer, the interaction of the reference cantilever with the sample comprising the analyte corresponds to the interaction of the test cantilever with the same sample not comprising the analyte.

Reference cantilevers according to the prior art, in contrast, only have no receptor layer which responds sensitively to the analyte. The reference cantilevers according to the prior art are also referred to as “inert”. They do commit determination of effects such as turbulence in the sample and the thermal drift of the sensor system. With a reference cantilever according to the prior art of this kind, however, the analyte may bind to the reference layer of the reference cantilever as a result, for example, of nonspecific binding. Because of this, however, the analyte itself contributes to the background noise. In the case of a sensor according to the prior art, therefore, reference measurements in a reference sample are necessary, this being a sample without analyte. Only in this way is it possible to determine the effect of the nonspecific binding of the substances which are not the analyte.

In this case of the sensor proposed here, the selective non-reception of the analyte by the reference cantilever drastically simplifies the measurement method, since the reference cantilever is not sensitive to the analyte and therefore the analyte also makes no contribution to the background noise. Here, only the substances which are not the analyte contribute to the background noise of the reference cantilever. To a certain extent, through the selective non-reception of the analyte on the reference cantilever, it is possible to ensure that the reference cantilever is subject to the same turbulences, the same thermal drift and the same influence by all the substances which are not the analyte as the test cantilever, and also as in a reference fluid. The difference, however, is that the reference signal is determined directly in the sample fluid.

In other words, there is no longer any need to calibrate the reference cantilever in a defined reference sample; instead, the measurement with test cantilever and reference cantilever can be carried out directly in the sample to be analyzed.

In particular, a reference cantilever with reference layer and a test cantilever with receptor layer produce a significantly more specific analysis of the analyte than just a reference cantilever without a receptor layer, since both the reference layer and the receptor layer exhibit specific interaction or non-interaction with the analyte.

Since the active transducers are arranged on the deformable parts of the cantilevers, it is possible, using the active transducers, to find a metric which corresponds to the strength of the interaction of the analyte with the deformable part. The passive transducers, conversely, are arranged on the bases of the cantilevers, and so the interaction is reduced to those interactions that do not primarily bring about deformation of the deformable part.

The structure of the sensor with reference cantilever and test cantilever has the advantage that it is possible to perform two measurements simultaneously in the sample, with the measurement by the reference cantilever able to calibrate the measurement by the test cantilever. As a result, it is possible to reduce ambient influences, for instance chemical, thermal, mechanical, electrical and fluidic interfering influences, on the respective measurement, and so the incidence of the analyte can be concluded from the comparison of the measurement on the test cantilever and on the reference cantilever.

In particular, it is also possible to optimize the geometric configuration of the reference cantilever with regard to a particular interfering influence. It is, moreover, also possible to determine different interfering influences with different reference cantilevers.

The transducer may be embodied and configured to ascertain deformations of the deformable parts of the test cantilever and of the reference cantilever, preferably to detect the forces exerted on each of the bases and the deformable parts of the test and reference cantilevers during the deformation.

If a sensor consisting of a reference cantilever and a test cantilever, with the reference layer and the receptor layer, respectively, is exposed to a sample which comprises an analyte, then the interaction may consist of the binding of the analyte to the receptor layer.

As a result of the binding of the analyte to the receptor layer, a force acts on the test cantilever, whereas no force acts due to the analyte on the reference cantilever. The force on the test cantilever increases more rapidly, for example, the greater the concentration of the analyte in the sample or the more quickly the surface of the cantilever is covered with the analyte. A maximum force possible for the respective embodiment is achieved when the cantilever is fully covered.

This interaction may result in a deformation of the deformable part of the test cantilever, while the deformable part of the reference cantilever is not bent. The basis for the deflection of the cantilever is the change in the surface stress caused by the interaction with the analyte. The change in the surface stress leads to a stretching or contraction of the upper (or lower) surface of the cantilever. The different stretching or contraction on upper and lower surfaces produce an internal force or physical stress in the material that leads to the deformation.

These forces or physical stresses, stretching or contractions for example, may ultimately be detected by the transducer, where stresses of different extent are detected by the transducer through stretches or contractions of different extent.

The force to be detected may be a bending force and/or a stretching force and/or a shearing force and/or a contraction force and/or may be due to the elasticity modulus of the reference cantilevers and test cantilevers.

A bending force may bring about an alteration in the geometry of the cantilever, and more particularly may impress on the cantilever a curvature which differs from the unstressed cantilever. Such curvature may lead to the occurrence of bending moments and therefore to bending stresses or stretches or contractions, which can be determined using a corresponding transducer.

A stretching force or contraction force may in particular bring about a change in length of the cantilever. The respective change in length may be different according to the direction of the crystal lattice of the cantilever.

The stretch (or contraction) may in particular be different at the upper surface from the lower surface of the cantilever. The stretching of the surface may take place in particular parallel to the base of the cantilever (a so-called transverse stretch) or perpendicular to the base of the cantilever (so-called longitudinal stretch). The magnitude of the stretch here is heavily dependent on the geometry and the crystal structure of the cantilevers and also of the further layers provided on the surfaces, such as the electrodes, for example, and so optimal detection of the analyte may be achieved through optimization of orientation and cantilever geometry.

Preferably, the relative deformation and/or the relative alteration in the surface stress runs in a transverse direction (i.e., in the direction of the transverse stretching) of the test cantilever and/or of the reference cantilever, with the transverse direction running parallel to the base of the test cantilever and/or of the reference cantilever, where preferably the active and the passive test transducer and/or the active and the passive reference transducer are oriented in the transverse direction.

With further preference, the relative deformation and/or the relative alteration in the surface stress runs in a longitudinal direction (i.e., in the direction of the longitudinal stretch) of the test cantilever and/or of the reference cantilever, where the longitudinal direction runs perpendicular to the base of the test cantilever and/or of the reference cantilever, with preferably the active and the passive test transducer and/or the active and the passive reference transducer being oriented in the longitudinal direction.

Where the stretching force on the upper surface and the lower surface is different, the acting force is also referred to as shearing force.

In the case of a deflected cantilever, a bending force is active, since a curvature is impressed on the cantilever. As a result, the upper surface of the cantilever is stretched and this stretching is in particular greater than at the lower surface of the cantilever, and so overall a shearing force acts on the cantilever as well.

The forces stated above are all based on what is called the elasticity modulus of the cantilever. The elasticity modulus of the cantilever is a physical constant which is specific to the material used for the cantilever. Through selection of the material or material composition and/or through treatment of the material, it is possible to adjust the elasticity modulus within a certain range, allowing the effect to be measured for the respectively configured transducers to be optimized. Conversely, it is of course also possible to adapt the transducers to the existing elasticity modulus of the material and to optimize their sensitivity.

Preferably, the cantilevers may be so called bimaterial cantilevers, examples being cantilevers composed of a gold layer and a silicon nitride layer. A bimaterial cantilever consists of material layers which together have a defined state of stress. The state for example may be stress-free, and so the intrinsic mechanical stresses are minimal. It may alternatively be the case that a bimaterial cantilever is prestressed, and so the cantilever responds particularly sensitively to a change in the surface stress. It may also be the case, however, that a homogeneous cantilever is coated differently on the upper side and the lower side, in order to imitate the bimaterial effect described.

Comparing the forces and/or deformations detected by the transducers makes it possible to conclude an effect, caused by the selective reception of the analyte, on the test cantilever, and thus the incidence of said analyte. Preferably, the magnitude of the incidence may be concluded.

In particular, the passive transducers on the bases of the cantilevers detect only effects which are primarily not deflection, since the bases are coupled fixedly to the substrate. The measurement signals from the passive transducers thus afford a base signal which is specific to the respective cantilever.

For example, the base of the reference cantilever, owing to influence by the ambient conditions, may bring about a first electrical state of the passive reference transducer, while the interaction of the test cantilever with the sample brings about a second electrical state of the passive test transducer.

Conversely, the active transducers on the deformable parts of the cantilevers indicate an extent of the deformation or acting force and hence also indirectly an extent of the interaction of the reference layer or receptor layer with the analyte and the other substances in the sample.

For example, through interaction with the sample, the reference cantilever may be bent by a first amount, and so the deflection brings about a third electrical state in the active reference transducer, whereas the test cantilever, through interaction with the sample, is bent by a second amount and is bent by a third amount through additional interaction with the analyte in the sample, this bringing about a fourth electrical state in the active test transducer.

Comparing the electrical states of the passive and active transducers indicates an extent of the deformation of the cantilevers, where the electrical signal from the active transducers is calibrated to the base signal from the passive transducers on the base. At the same time, a comparison of the active transducers, or of the measurement signals from the active transducers, provides an extent of the difference between the deformation of the cantilevers. As a result it is possible to derive a specific influence of an analyte on the test cantilever.

The construction with four transducers has the advantage that such local calibration of the sensor is possible at the site of the influence of the sample and of the analyte.

The deformable parts of the reference and test cantilevers may have identical geometry dimensions, where preferably the width of the deformable part of the reference and test cantilevers corresponds to the length of the deformable part of the reference and test cantilevers, where more preferably the deformable parts of the reference and test cantilevers are less than 100 μm wider, less than 100 μm long and less than 1 μm thick, more particularly 50 μm wide, 50 μm long and 0.3 μm thick.

This makes it possible to generate a particularly high force through the deformation of the cantilevers on the active transducers.

The bases of the reference and test cantilevers may be arranged on the same overall base, such as on the same substrate, for example.

This makes it possible for the passive transducers to operate on a similar basic level, or to reduce influences that would be specific for separate bases. The arrangement on the same overall base may therefore result in a greater measurement accuracy.

As a result, the reference and test cantilevers may in particular be arranged especially close to one another, at a distance, for example, of less than or nearer than the width of a cantilever.

In this way it is possible for the two cantilevers to be subject to identical interfering influences, which are caused, for example, by a temperature difference in the sample, in particular by convection or another fluid dynamic.

It is also possible as a result, furthermore, for two or more cantilevers to be able to be produced from one (silicon) wafer. This enables cost-effective production of the sensor.

Furthermore, the distance of the cantilevers from the production limit may also be optimized. The production limit is typically defined by the spotting distance, with the spotting distance being a metric that is relevant when producing the reference and receptor layer; see below.

The bases of the reference cantilever and of the test cantilever may be formed as one piece with one another.

As a result it is possible for the base-specific influences to be further reduced, achieving a greater measurement accuracy. It also enables the possibility of easier production of the cantilever pair or of a multiplicity of cantilever pairs.

The reference and test cantilevers may comprise Si3N4, SiO2, Si3N4/SiO2, SiC, Si or consist of Si or comprise a polymer. Equally, the bases and/or the overall base may also comprise the stated materials. The bases and the reference and test cantilevers may also be produced in one piece with one another from the stated materials by conventional production operations of the kind known for the processing of wafers.

As a result of the silicon-based reference and test cantilevers, it is possible to use production methods known from the semiconductor industry, allowing sensors of the invention to be produced on a large industrial scale. Polymers may likewise be produced on a large industrial scale and have the advantage that their physical properties can to a large extent be predetermined.

The transducers may have identical intrinsic physical properties, with the transducers being configured to adapt their electrical properties, preferably the electrical resistance or another value proportional to the k value, in accordance with the forces acting on the reference and test cantilevers.

The k value, also called gauge factor is the proportionality constant between the stretching of the transducer and its change in resistance:

$$\frac{\Delta R}{R} = k\frac{\Delta L}{L},$$

where ΔR is the change in resistance of the transducer, R is the resistance of the transducer with the unbent cantilever, ΔL is the change in length of the transducer, and L is the length of the transducer with the unbent cantilever. In particular, it is also possible to measure all other parameters proportional to the k value or to the resistance, such as the conductivity, for example.

Identical intrinsic physical properties here comprise those properties responsible for the measurement properties of the transducer on a cantilever. This concerns in particular a voltage that may drop across the transducer, in other words the resistance or the conductivity of the transducer. The resistance is dependent in particular on the geometry of the transducer, and so, in the case of uniform conductivity of the various transducers, the geometry of the transducers, accordingly, must be the same.

The physical properties also, however, relate to the nature of the change in measurement signal in response to an acting force. The intention in particular is that each transducer responds identically to an identical exerted force or deformation of the cantilever, so that there can be no nonlinear deviations occurring between the various transducers.

The intrinsic physical properties are determined in particular by the nanostructure of the transducers. The nanostructures are preferably identical for all the transducers, and so identical geometrical configurations yield identical physical properties.

This may be achieved in particular by minimizing the grain size of the metal particles in the transducers.

Through a reliable production process for the transducers, therefore, it is possible to ensure that all the transducers respond identically to a force, and so deviations in the various measured forces are due solely to the external activity on the cantilevers and are not dependent on the intrinsic physical properties.

The electrical properties of the transducers may ultimately be used in particular to derive the bending states of the individual reference and test cantilevers, allowing conclusions to be drawn in particular about the incidence of the analyte selectively received by the receptor layer. The transducers, which perceive interaction with the analyte indirectly via the cantilever, vary their measurement properties in accordance with the acting forces.

The distance between the active reference transducer or test transducer and the passive reference transducer or test transducer, respectively, may be less than 100 μm, and the transducers may lie against the bending edge.

By placement of the transducers as close as possible to one another, spatial influences on the transducers, originating from the sample, are reduced. If, for example, the incidence of the analyte in the sample is subject to a certain concentration gradient, it is advantageous to carry out the measurements as far as possible at one point in the gradient.

The minimum distance is achieved when the transducers lie against the bending edge. The bending edge in this context is that edge of the substrate along which the cantilevers are divided into the base and the deformable part. For example, the active transducers may lie with their lower edge against the bending edge, whereas the passive transducers may lie with their upper edge against the bending edge.

The optimum distance between the active transducers and the bending edge may be dependent in particular on the precise geometrical shaping of the sensor. Accordingly, the distance to the bending edge may be selected such that a surface stretching generates a maximum change in the electronic state of the transducer.

The optimum distance between the passive transducers and the bending edge is achieved in particular if the deflection of the test cantilever produces an extremely small change in the electronic state of the test transducer.

In particular, however, the active and passive transducers ought to be arranged so close to one another that in a production operation, such as in a scanning electron microscope-based production operation, they can be written together easily and quickly in one step, without any need for the wafer to be displaced by a mechanical movement of an XYZ advancement device. In this way it is possible in particular to enable a much more rapidly and more precise—and also cost-effective—production of the sensors.

The orientation of the transducers determines in particular whether a longitudinal or a transverse stretching of the cantilevers is measured. If a longitudinal axis of the transducer runs parallel to the base, then preferably a transverse stretching of the cantilever is measured. If a longitudinal axis of the transducer is oriented perpendicular to the base, then preferably the longitudinal stretching of the cantilever is measured. It is therefore also possible in particular to shape rectangular, square, round or oval transducers in order to adapt the sensitivity of the transducer to the cantilever geometry.

The reference and test cantilevers, and also the active and passive reference and test transducers, may be arranged mirror-symmetrically to one another.

The mirror symmetry may relate in particular to a mirror axis arranged between the reference transducer and the test transducer.

Through a mirror-symmetrical construction it is possible to reduce influences of electrical voltages, for example, on the transducers, or at least to route them symmetrically to one another. This makes it possible to improve the measurement accuracy and susceptibility to inference.

The sensor may have electrodes, and may preferably have four electrodes, which are configured to electrically contact the transducers.

An electrode in this context is a conductive layer, composed of gold, for example, or a wire or cable that is able to produce an electrically conductive connection from one connection end of the transducer to an external device, such as a current source or voltage source, for example, or to a corresponding measuring device. In principle any conductive connection between the transducer and the external device may be understood as an electrode. Here, however, the electrode is considered more particularly to be that part of the electrical connection that is realized on the sensor.

An electrical connection from the sensor to an external source or a measuring device is typically realized via an electrical connection. In this case an electrical connection plug having a cable or a wire is contacted to a so-called bonding pad, in which, for example, the wire is firmly welded using ultrasound. From the bonding pad, an electrical connection then leads directly to the transducer. The electrical isopotential surface between the transducer and the bonding pad is referred to below as the electrode.

The purpose of the electrode is to contact the transducers electrically and in particular to provide the option of routing the electrical signals from the sensor to a measuring device.

The electrodes may in particular be at different electrical potentials and may interact with one another via these potentials. In order to minimize this mutual influencing of the electrical currents and voltages in the electrodes, it is therefore advantageous if the electrodes likewise have a symmetrical shape, so that the respective interference is at least distributed evenly over the system as a whole. This may be achieved in particular by using an even number of electrodes, or only four electrodes in the case of four transducers.

Through the design of the electrode geometry, therefore, it is possible for the base signal level that arises at the electrodes due to any potential differences to be less than 1.1 V, and so there is no need for the electrodes to be electrically encapsulated. Electrical encapsulation in this context may refer, for example, to electrical insulation or masking or shielding of the electrodes and of the bonding wires. As a result, the production operation can be simplified—the measurement accuracy is improved.

The distance between the electrodes may be minimal.

Minimal in this context is the distance when the electrodes are not touching, meaning that they are not conductively connected to one another. In other words, the conductance between the electrodes is substantially lower than the conductance of the transducers.

With the distance between the electrodes being minimal, it is possible for more electrodes to be sited on a wafer, thereby enabling a cost-efficient production operation. This also makes it possible, however, in particular to reduce the size of the transducers, enabling a further reduction in the effect of uneven ambient conditions on the transducers.

The transducers may be electrically interconnected in a full bridge, where the full bridge is configured to develop a transverse bridge voltage because of the electrical properties of the transducers, more particularly in the case of an asymmetrical change in the electrical properties of the transducers.

A full bridge in this context is a measuring facility for measuring electrical resistances or small changes in resistance. Other terms for a full bridge are Wheatstone measuring bridge, H bridge, symmetrical full bridge, and thermal-symmetrical full bridge.

For example, the active and passive transducers of the reference and test cantilevers are interconnected to form a full bridge in that each connection contact of the active transducers is set to a common potential via a first electrode. A respective connection contact of the passive transducers, furthermore, is set to a common potential via a third electrode. A voltage (DC or AC voltage) may be applied via these first and third electrodes, with the combination of the active transducers or the passive transducers acting respectively as a voltage divider in accordance with the resistances of the respective transducers.

Moreover, on each cantilever, the further connection contact of the active transducer is connected to the further connection contact of the passive transducer via a second electrode in the case of the test cantilever or fourth electrode in the case of the reference cantilever. Via the second and fourth electrodes, correspondingly, a transverse bridge voltage is developed, provided that the ratio of the resistances of the active transducer to the passive transducer of the reference cantilever is not equal to the ratio of the resistances of the active transducer to the passive transducer of the test cantilever.

In the basic state of the full bridge of the sensor, the transverse bridge voltage is ideally zero, since there is no force or an identical force acting on all of the transducers involved. This basic state is preferably established during the production operation itself, so that only a slight offset voltage, which can be compensated by way of a metrological construction, is established between the electrodes.

Starting from this basic state of the full bridge, it is then possible to detect preferably asymmetrical force changes. If, for example, the active test transducer of the test cantilever responds to an exerted force with a change in its electrical property or with a change in its electrical resistance, then the ratio of the resistances in the full bridge is no longer balanced, and so a transverse bridge voltage is developed. The transverse bridge voltage developed can ultimately be detected using a measuring device.

In particular, no transverse bridge voltage is developed if the exerted force on the active transducers of the test cantilever and of the reference cantilever is the same. In that case, however, this is a nonspecific exerted force which does not originate from a specific interaction with the test cantilever. In particular, no transverse bridge voltage is developed, either, if the exerted force on the passive transducers of the test cantilever and of the reference cantilever is the same.

Via the realization as a full bridge, the active test transducer of the test cantilever is calibrated, so to speak, by the active reference transducer of the reference cantilever. The passive transducers on the one hand enable calibration to the basic state of the full bridge, and on the other hand a deflection of the deformable parts of the cantilevers may be derived from comparison of the active and passive transducers.

The sensor may comprise a transverse bridge voltage detector which is configured to detect the transverse bridge voltage of the full bridge, where the incidence of the analyte selectively received by the receptor layer, and preferably the magnitude of the incidence, is derived from the transverse bridge voltage detected.

A transverse bridge voltage detector may more particularly be any detector which is capable of detecting a voltage. It may for example be a measuring resistor, or a signal transmitter or a measuring device that indicates the voltage, or another kind of detector that generates an output signal through the detection of a voltage.

The transverse bridge voltage detector may be configured to generate a single output value, and so only the incidence of a transverse bridge voltage is indicated. The incidence of a transverse bridge voltage may in particular be taken as a basis to conclude that an analyte at a certain minimum concentration has interacted with the receptor layer of the test cantilever, and consequently the electrical properties of the transducers, or at least the electrical property of the active transducer of the test cantilever, have altered.

However, a transverse bridge voltage detector may also indicate different output values, which preferably have a simple functional relationship with the transverse bridge voltage. This may mean, for example, that the output value with the transverse bridge voltage detector rises if the transverse bridge voltage rises. It may, however, also mean that the output value of the transverse bridge voltage detector drops if the transverse bridge voltage rises. It is particularly advantageous if the output value of the detector can be used to conclude an unambiguous value of the transverse bridge voltage. In other words, it is preferable if the output value from the transverse bridge voltage detector follows a bijective function of the transverse bridge voltage.

The change in the bridge voltage is ideally expressed as a ratiometric change in relation to a defined, i.e., measured, supply voltage. In that case, for example, a drift in the supply voltage does not influence the measurement signal.

The various output values need not be confined to the amplitude of the signal, but may instead also be confined to the temporal occurrence of the output value. For example, the transverse bridge voltage detector may emit one pulse per time interval in the case of a first voltage, whereas in the case of a second voltage the transverse bridge voltage detector emits numerous pulses per time interval. The occurrence of the pulses may therefore be used to indicate the strength of the transverse bridge voltage. In particular, therefore, the output value may be coded.

The electrical properties of the transducers may be output via an A/D converter and an A/D converter logic unit may be configured to provide a differential measurement and/or an absolute measurement of the bending states.

The transverse bridge voltage detector may be designed more particularly in the form of an A/D converter, where an A/D converter is a converter electronic unit that generates a digital signal from an analog signal. For this purpose, for example, the strength of the measurement signal is sampled locally with a certain periodicity by the A/D converter, and the measured voltage is converted into a digital value.

The A/D converter may in particular comprise an A/D converter logic unit, with the AM converter logic unit being able to be put into different operating modes through adjustment of the internal circuitry, more particularly through software adaptations. By way of the different operating modes, different voltages (especially AC voltages and/or DC voltages) and measurement signals may be tapped off from the electrode circuit.

The A/D converter for example may have what is called a differential measuring mode, in which only the change in bending state between the reference cantilever and the test cantilever is detected. In this differential measuring mode, the transverse bridge voltage in particular is tapped off, and so a change in the bending states of the cantilevers is detected in the form of an occurring transverse bridge voltage. The differential measuring mode is the preferred measuring mode for detecting binding of an analyte to the receptor layer.

It is, however, also possible to operate the A/D converter in what is called an absolute measuring mode, in which the individual transducers are accessed directly via the electrodes (single-ended mode). This enables measurement of the individual transducer resistances, for the purpose of quality assurance, for example, or else for characterizing the full bridge. Yet a further possibility is to detect the absolute bending states of the cantilevers.

With this construction, in particular, only one A/D converter is needed, and so the production operation can be realized cost-effectively.

Moreover, owing to the stable and balanced full bridge, it is also possible to remove the A/D converter far away from the actual transducers and cantilevers, and so, for example, any heat given off by the A/D converter does not influence the measurement outcome.

The sensor may be embodied on a chip.

This may mean that the sensor is produced on a semiconductor structure which allows more in-depth data processing of the transverse bridge voltage or of the output value from the A/D converter logic unit. A chip may also refer in particular to a so-called system-on-a-chip, where all of the functional units of the measurement system are embodied integrally on a single electronic component.

It should, however, be borne in mind that the operational chain for the production of the sensor may comprise gold, and this may adversely affect the production of an A/D converter logic unit using CMOS semiconductor technologies.

A multiplicity of cantilever pairs may be arranged on a chip, in which case an A/D converter logic unit may be configured to provide signal multiplexing of the measurement signals.

Each cantilever pair comprises a reference cantilever and a test cantilever. A multiplicity of such cantilever pairs may be arranged on a chip, together with active and passive transducers, and may in turn each be able to be read via an A/D converter logic unit.

It may also be the case in particular that a first cantilever pair responds specifically to a first analyte and a second cantilever pair responds to a second analyte, allowing different analytes to be detected simultaneously with a sensor.

A multiplicity of cantilever pairs may also comprise a first number of test cantilevers and a second number of reference cantilevers. For example, the various reference cantilevers may detect different interfering influences with particular sensitivity with these together delivering the reference for the number of test cantilevers.

The cantilever pairs may be operated simultaneously using an appropriate A/D converter logic unit. As a result it is possible on the one hand to detect numerous different analytes by means of different receptor and reference layers. On the other hand, however, it is also possible, using identical receptor layers and reference layers, to establish a statistical statement regarding the significance of the measured transverse bridge voltages.

The upper surfaces of the reference and test cantilevers may have been activated by an activation layer, with the activation layer being configured, in the case of a force exerted on the reference and test cantilevers, to provide a greater surface stretching in comparison to the unactivated lower surface of the reference and test cantilevers, with the activation layer comprising gold or other chemically inert materials.

Activation of the upper surface may mean that the application of an activation layer provides adhesion for a further layer. The reason for this may be that the base material of the cantilever does not, for example, enter into any binding with the further layer, more particularly the reference layer.

The activation layer may in particular comprise gold, or consist entirely of gold.

Preferably the complete surface of the cantilevers is covered with gold, as the receptor layer is preferably constructed on the gold layer. Accordingly, an extensive layer with the activation layer may also cover a larger area with the receptor layer, so producing a large detector area for the analyte. As a result of the large detector area for the analyte, this in turn results in a particularly large deformation of the cantilevers, and so sensitive detection of the incidence of the analyte is possible.

With the upper surface having an activation layer, the construction of the cantilevers in terms of height is, in particular, nonhomogeneous or asymmetric, instead consisting of layers. This allows the elasticity of the cantilever to be critically influenced, and so on the upper surface in the event of deformation of the cantilevers there is a greater surface stretching, leading in turn to a larger measurement signal.

Because of the effective conductivity, coating of the cantilevers with gold may likewise be used to form electrodes for the transducers. For this reason, the distance between the electrodes may also be minimized, as in this way very little of the area of the cantilever is not covered with gold. Accordingly the detector area selected may be large.

The activation layer may in particular also consist of a chromium-gold alloy, since in this way the mechanical properties of the cantilever are less influenced. A particular effect of the admixing of chromium is to make the crystallites in the gold layer homogeneous, meaning that any disruptive anisotropic effects caused by the crystal lattice of a hypothetical crystalline layer can be avoided.

The lower surfaces of the reference and test cantilevers may have been passivated by a passivation layer with the passivation layer being configured to minimize any unspecific adhesion of protein to the reference and test cantilevers, and with the passivation layer comprising trimethoxysilane and/or a blocking substance.

In contradistinction to an activation layer, a passivation layer is a layer whose purpose is to minimize or prevent any interaction between the cantilever and another material. As a result of this, during the production of the receptor layer, the latter binds only to the upper surface of the cantilever and not to the lower surface of the cantilever. As a result, through binding of the receptor layer with an analyte, a greater surface stress can be achieved at the upper surface. Additionally, as a result, the asymmetry of the layer structure is enhanced, leading possibly to improved stretching properties for signal detection.

Materials particularly suitable for the passivation of the lower surface are trimethoxysilane and also what are called blocking layers. This passivation layer minimizes so-called unspecific protein adhesion. Protein adhesion is the adhesion of a protein on the surface. Unspecific adhesion of a protein or of a substance in general to the cantilever may lead to distortions of the measurement, as these unspecific substances likewise interact with the cantilever. By preventing this unspecific adhesion, there is an increase in the relative influence of the desired specific adhesion or interaction of the analyte with the cantilever, relative to the basic state of the cantilever.

It is, however, also possible for a passivation layer to bind the analyte as well, but in such a way that the resultant surface stress is opposite to the surface stress of the activation layer. This makes it possible to achieve greater deformation of the cantilevers.

The so called blocking layer may be adapted in particular to the respective analyte under investigation, in order to define a measurement window for the analyte. The blocking layer in this case is applied by a so called spotting or washing process.

In the case of the washing process, a so-called "sealer" protects the hydrate envelope of the detector proteins during drying and so makes them storable. The sealer is incorporated solubly in a matrix, and so is soluble for a sample fluid such as water. Moreover, the sealer has a certain layer thickness, and so the cantilevers are mechanically stabilized, which increases protection during storage of the cantilevers. A sealer may comprise sugar, for example. The sugar crystals are hydrophilic and therefore protect the hydrate envelope of the proteins. Accordingly a so-called reconstitution of the proteins, where the dried proteins are reactivated in the measuring fluid, is possible.

In the case of spotting of the receptor proteins, so-called "buffers" are utilized in order to enable reconstitution of the proteins in the sample fluid. Here as well, the shelf life of the sensors is increased by drying.

The active cantilever and the passive cantilever may have chemically identical construction.

The effect of this is that the measurement signal, especially in the case of a differential measurement of the transverse bridge voltage, is based solely on the influence of the analyte on the cantilever, and is not brought about by other properties of the cantilevers.

The chemical identical refers in particular to the fact that the cantilevers are altered and adapted to the extent that they differ only in terms of their binding properties or interaction properties with respect to the analyte under measurement. For all other substances, the aim is to achieve interaction that is as far as possible the same, or to achieve minimal interaction.

For this purpose, the reference cantilever and the test cantilever have an identical layer construction, which differs only in that on the test cantilever a receptor layer is applied and on the reference cantilever a reference layer. The chemical intensity therefore means, in particular, that the two cantilevers differ only in the reference layer or test layer, respectively.

All in all, the overall layer structure of the cantilevers as described above may also be inverted. This means that the reference and receptor layers, instead of being applied on the upper surface, may also be applied on the lower surface of the cantilevers. For example, the receptor layer may also be arranged on the lower side of the cantilever.

In order for the cantilever to deform, any chemical attachment to the cantilever ought ideally to occur on one side. If the analyte binds on the upper side, their ought to be no unspecific binding on the lower side of the cantilever, since otherwise the surface stress resulting from the chemical binding of the analyte may be compensated by the unspecific chemical binding on the lower side of the cantilever.

In other words, the chemical attachment on the upper side and the lower side must at least be asymmetrical in order to achieve deformation. A greater attachment on the upper side than on the lower side, or a greater attachment on the bottom side than on the upper side, results, correspondingly in a measurable deformation of the test cantilever.

The reference and test cantilevers may have a further layer which comprises a self-assembling monolayer.

A self-assembling monolayer may, in particular reduce unevennesses on the gold surface, enabling uniform coating of the cantilevers with the receptor layer or reference layer, respectively. As a result of the homogeneous surface properties of the cantilevers, it is ultimately possible in this way to improve the binding properties of the receptor layer and of the analytes.

The receptor layer may comprise antibodies for an antigen, and the reference layer may comprise an antigen-specific isotype control antibody according to the antibody of the reference layer.

Antibodies are proteins which are produced by body cells as a product of response to antigens. Antibodies are typically used by the human immune system to bind to the antigens of viruses, so that the viruses are labeled and an outbreak of a viral infection can be avoided by the immune system. It may in particular be the case that an antibody binds to different antigens, so that the specificity of the antibody is reduced.

In contrast to this, an isotype control antibody binds specifically not to the antigen of a virus, and so, in the event of the simultaneous presence of binding of the antibody to the antigen and lack of binding of the isotype control body to the antigen, the presence of a particular virus or antigen of a virus can be concluded with a high specificity.

The antibody of an antigen may be part of the receptor layer of the test cantilever, while the isotype control antibody of the antigen may be part of the reference layer. An advantage of this is that deflection of the test cantilever may be confirmed at the same time by non-deflection of the reference cantilever.

The reference layer and receptor layer of the cantilever may additionally have the so-called protein A for better adhesion of the antibodies, this protein binding covalently to the self-assembling monolayer.

The layers may be produced in a dipping/spotting process, in which case the spotting may be carried out preferably by means of commercially available machines. In this case, droplets of the respective layer are deposited on the cantilever, so that a spatial limitation of the functionalization is achieved, so enabling, in particular, a cost-effective and independent coating of the cantilevers. The very small drops are hindered from drying by appropriate control of the ambient parameters, such as temperature, air humidity and dew point. The lower sides of the cantilevers are not activated here, and so the antibodies used make contact solely with the upper surface of the cantilever. The layers are then dried, and so an elevated or reduced temperature has little or, preferably no influence on the antibodies. This enables a long shelf life, especially in an inert gas. The protein layers are applied in particular after the application of the transducers but before the sensors are singulated from the wafer.

The receptor layer may comprise Sars-CoV2 antibodies and the reference layer may comprise Sars-CoV2-specific isotype control antibodies.

The Sars-Cov2 antibody preferably binds to the S1 or N antigen of the Sars-CoV2 virus. The antibody is monoclonal and sequence-accurate and has a high specificity for the Sars-CoV2 antigen. The antibody may be produced in particular by the method known as phage display. Conversely, the Sars-CoV2-specific isotype control antibody may have ultrahigh specificity for the corresponding antigen, while being otherwise identical with the active antibody.

As a result, rapid detection of the Sars-CoV2 antibody, for example, is possible. The electrical measurement and the accumulation of the antibodies on the test cantilever, in particular, result in a rapid test method which, by virtue of comparison with the non-accumulation on the reference cantilever, also has a high specificity.

The receptor layer may in general provide molecule-specific binding forces, and the reference layer provides molecule-specifically no binding forces. As a result it is possible to detect a particular molecular species.

The receptor layer may comprise single-strand DNA (ssDNA) and/or other DNA fragments, able to bind specifically to DNA fragments in the sample. The reference layer may comprise single-strand DNA and/or other DNA fragments not binding to any chemical and/or biochemical and/or physical species in the sample, but coinciding with the receptor layer in characteristic parameters (e.g., chain length, chemical construction).

The receptor layer may comprise single-strand RNA and/or other RNA fragments, able to bind specifically to RNA fragments in the sample. The reference layer may comprise single-strand RNA and/or other RNA fragments not binding to any chemical and/or biochemical and/or physical species in the sample, but coinciding with the receptor layer in characteristic parameters (e.g., chain length, chemical construction). As a result it is possible to detect a particular DNA or RNA and also fragments thereof and/or other oligonucleotides.

The receptor layer may comprise antibodies and/or other and/or further proteins which are able to specifically bind target proteins, and the reference layer may correspondingly comprise specific isotype control antibodies and/or further proteins that do not bind to any chemical and/or biochemical and/or physical species in the sample.

The receptor layer may comprise scFv antibodies and the reference layer may comprise scFv antibody-specific isotype control antibodies. An scFv antibody is an artificially produced antibody fragment. Breaking down an antibody into multiple fragments allows the responsiveness of the sensor to a low sample concentration to be enhanced.

The receptor layer and/or the reference layer may comprise hydrogels.

Hydrogels are molecular matrices that are able to bind water very well and that swell up to a great extent on contact with water. Through chemical modification of the hydrogels, especially the matrix, it is possible to bring about a strong response by the hydrogel to the presence of antibodies, so multiplying the mechanical deformation of the cantilever. In particular it is also possible in this way to carry out a pH-sensitive measurement of the analyte.

BRIEF DESCRIPTION OF THE FIGURES

Preferred further embodiments of the invention are elucidated in more detail below by the following description of the figures, in which.

DETAILED DESCRIPTION OF EXEMPLARY EMBODIMENTS

In the following, preferred embodiments are described with reference to the figures. Here, elements that are identical, similar or have the same effect are provided with identical reference signs in the various figures, and in some cases a repeated description of these elements is omitted in order to prevent redundancies.

Figure 1:
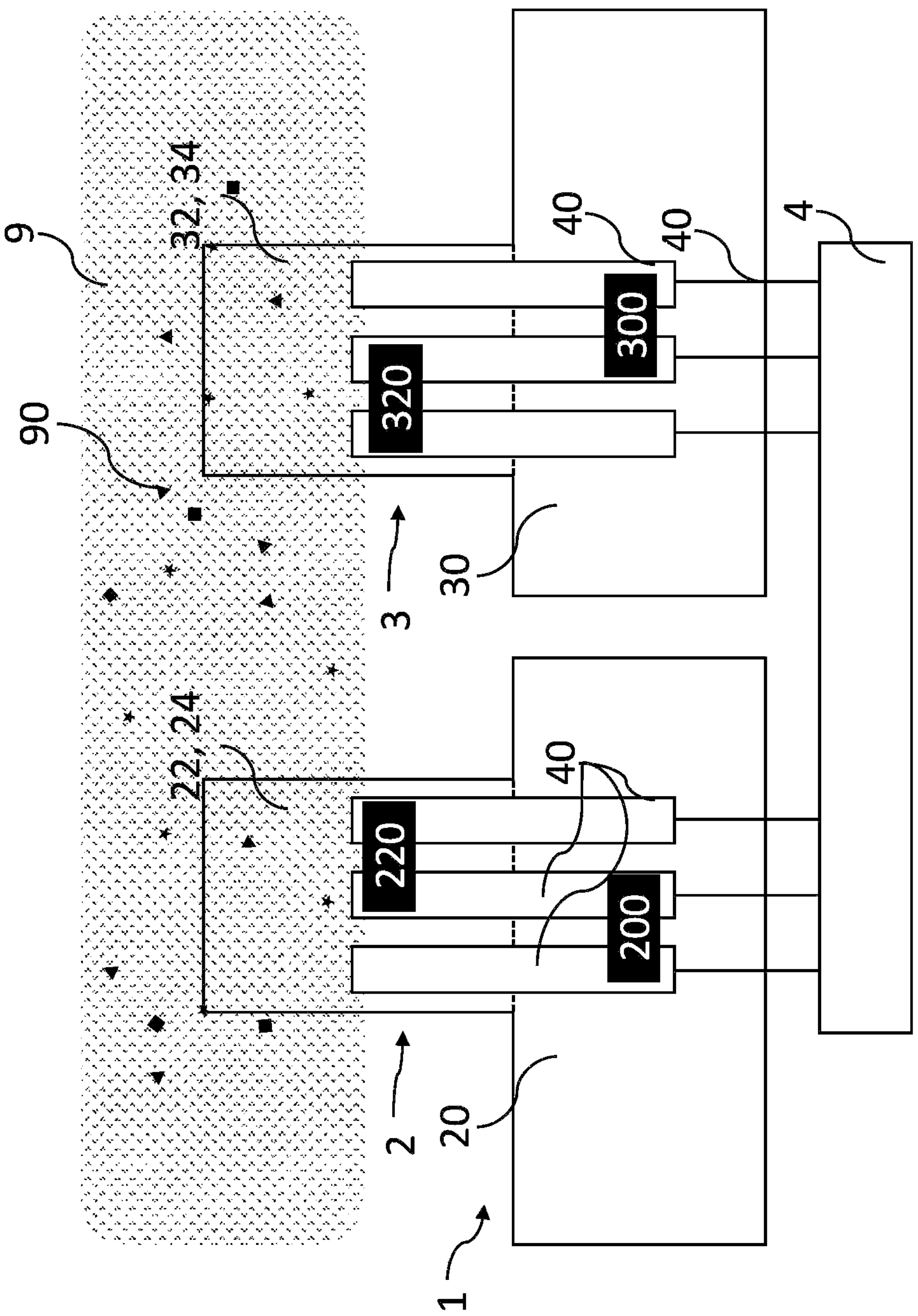
FIG. 1 shows a schematic representation of a first embodiment of the sensor.

FIG. 1 schematically shows a first embodiment of the sensor 1 of the invention for converting chemical and/or biochemical information. The sensor 1 comprises a test cantilever 2, which has a base 20 and a deformable part 22.

Arranged on the base 20 is a passive test transducer 200, whereas an active test transducer 220 is arranged on the deformable part 22. In analogy to this, the sensor 1 also has a reference cantilever 3, which in turn has a base 30 with a passive reference transducer 300, and a deformable part 32 which has an active reference transducer 320.

The transducers 200, 220, 300, 320 are each connected via electrodes 40 to an electronic unit 4 which is capable of recording or transmitting a measurement signal from the transducers 200, 220, 300, 320, while the electronic unit 4 is likewise capable of supplying the transducers 200, 220, 300, 320 with current and/or voltage.

The function of the sensor 1 is to indicate the incidence and preferably the amount of the incidence of an analyte 90 in a sample 9. In FIG. 1 the sample 9 is a fluid produced, for example, by treatment of a swab, more particularly a nasal swab or throat swab, from a test subject. It may also be the case, however, that the sample 9 is saliva or blood or another bodily fluid. It may also be the case, however, that the sample 9 is a gargling fluid that the test subject has gargled. It may also be the case that the sample 9 has been synthesized and/or obtained from a tissue sample or from another substance taken from the test subject. The analyte 90 in this case may be in solution in the sample, or may be present in undissolved form as a suspension or dispersion or emulsion.

In any case, the aim with the sensor 1 is to investigate the sample 9 for the incidence and/or concentration and/or amount of the analyte 90. For this purpose, a receptor layer 24 is applied on the test cantilever, and an analyte 90 is able to interact with this layer, or a receptor layer 24 is applied which is able to adsorb or absorb the analyte 90. In the case of adsorption, the analyte 90 would adhere on the surface of the receptor layer 24, while in the case of absorption the analyte 90 would penetrate the interior of the reference coating 90.

When the sample 9 contains an analyte 90, then, the latter is able to interact with the receptor layer 24. This may result in a change in the surface stress of that portion of the deformable part 22 of the test cantilever 2 that is coated with the receptor layer 24, so leading to a deformation of the deformable part 22 of the test cantilever 2. The active test transducer 220 therefore registers a deformation and/or alteration in the surface stress of the deformable part of the test cantilever 2, which is interpreted in turn in the electronic unit 4 as a measurement signal.

However, because of the interaction with the sample fluid 9, there may already be a deformation recorded by the active test transducer 220, for example by only the surface stress of the fluid acting on the deformable part 22 of the test cantilever 2 and causing it to deform. For a deformation of this kind, accordingly, it is not the presence of an analyte 90 that is responsible.

In order to establish the magnitude of this basic action of the sample 9 on the test cantilever 2, the reference cantilever 3 is contacted with the sample 9 at the same time as the test cantilever 2. For this purpose the reference cantilever 3 has a reference layer 34, with which an analyte 90 cannot interact, or a reference layer 24 which is unable to adsorb or absorb the analyte 90. In this case interaction with the analyte 90 is to be avoided, in order to enable differentiation relative to the measurement signal from the test cantilever 2.

With both the test cantilever 2 and the reference cantilever 3 interacting with the sample 9, the two cantilevers 2, 3 interact similarly with the sample 9. The difference in this case, however, is that the test cantilever 2 is additionally able to interact with any analyte 90 that is present, via its reference layer 24. Accordingly, the measurement signals from the active transducers 220, 320 differ if there is an analyte 90 in the sample 9. From the magnitude of the difference between the measurement signals, accordingly, it is possible in the simplest case to infer the amount of the incidence of the analyte 90 in the sample 9.

The test cantilever 2 and the reference cantilever 3 measure the incidence of the analyte 19 in the sample 9 at different positions, however. At different positions of the sample there may be different ambient conditions, such as, for example, temperature fluctuations or concentration gradients, etc.

These different ambient conditions can be measured with the passive transducers 200, 300. The passive transducers 200, 300 are arranged on the base and preferably do not detect any measurement signal in the case of a deformation of the deformable part 22, 32 of the reference or test cantilevers 2, 3 respectively. However, the base level of the measurement signal from the passive transducers 200, 300 may be influenced because of these different ambient conditions. By provision, for each measurement value of the active transducers 220, 320 via the passive transducers 200, 300, of a comparative value which looks at the ambient conditions in isolation, it is possible for the influence of the ambient conditions on the measurement signals from the active transducers 220, 320 to be determined and reduced and/or factored out or isolated.

The sensor 1 can be used accordingly to analyze the incidence of an analyte 90 in a sample 9 in isolation, by reducing and isolating the influence of interactions for which the analyte 90 is not held responsible, by means of a multiplicity of measurement points on the reference and test cantilevers 3, 2. This allows a high measurement accuracy of the incidence of the analyte 90 in the sample 9.

Figures 2A, 2B:
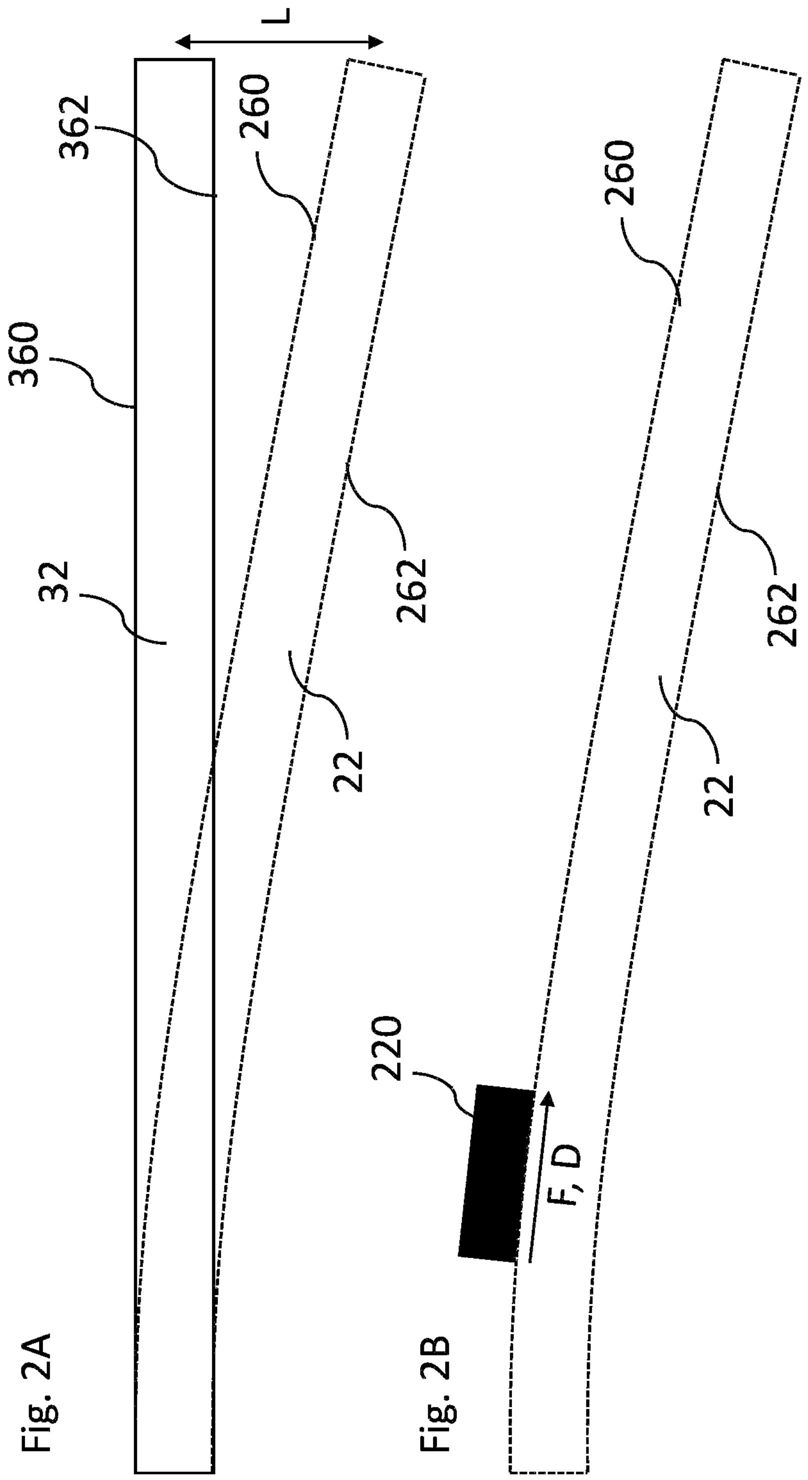
FIGS. 2A, B, C, D show a schematic representation of the cantilevers.

FIG. 2A shows the comparison of the deformable parts 32, 22 of the reference and test cantilevers 3, 2 in the event of a deformation and longitudinal stretching. The deformable part 32 of the reference cantilever 3 has an upper surface 360 and a lower surface 362. The deformable part 22 of the test cantilever 2 also has an upper surface 260 and a lower surface 262. Where an analyte 90 of the sample 9 interacts with the test cantilever 2 or with the receptor layer 24, there is a deformation of the deformable part 22 from the stationary part (which transitions into the base of the test cantilever) toward the freely movable part of the deformable part 22. The deflection L that is shown is a result in this case of the relative deflection between the deformable part 32 of the reference cantilever 3 and the deformable part 22 of the test cantilever 2, owing to the interaction with the analyte 90.

The deformation of the deformable part 22 of the test cantilever 2 is shown in FIG. 2B. The cause of this is that the upper surface 260 and the lower surface 262 of the test cantilever 2 stretch to different extents. Because of the large stretching D at the upper surface 260, an active transducer 220 applied thereon may register a stretching force F. The stretching force F registered may in this case be converted by the active transducer 220 into an electronic signal and/or may influence an existing electronics signal, such as an applied voltage, for example. This may be accomplished, for example, by the transducer changing the resistance if it experiences a stretching force F, resulting in turn in a stretching of the transducer 220.

The transducer could also detect a contraction of the surface on which it is arranged. In the embodiments shown, however, the transducers are always arranged on surfaces for which stretching is anticipated.

The stretching and/or alteration of surface stress and/or force that is detected by the transducer may alternatively be a bending force or a shearing force or may be caused by a bending force or shearing force or may generally be due to the elasticity modulus of the respective cantilever. In particular, as a result of the securement of the deformable part 22, 32 on the base 20, 30, the deformable part 22, 32, due to an action of force, is oriented along a bending curve by an alteration in the surface stress of the test cantilever. The resulting bending curve is a product in particular of the geometry, more particularly the surface moment of inertia of the cantilever, and also of the mass of the cantilever and the elasticity modulus. The bending curves may be described for example in accordance with beam theory.

As a result of the surface stresses which are different on the lower side and the upper side of the cantilever, the described deformation or stretching of the cantilever occurs accordingly.

Via beam theory it is possible for example to predict the point on the deformable part 22, 32 at which the stretching D is the greatest. It is possible to arrange the active transducer 220, 320 at this point in order to obtain an optimal signal-to-noise ratio and in order to respond as sensitively as possible to the stretches. In terms of the precise positioning of the transducers, however, other boundary conditions ought also to be taken into consideration.

Figure 2C:
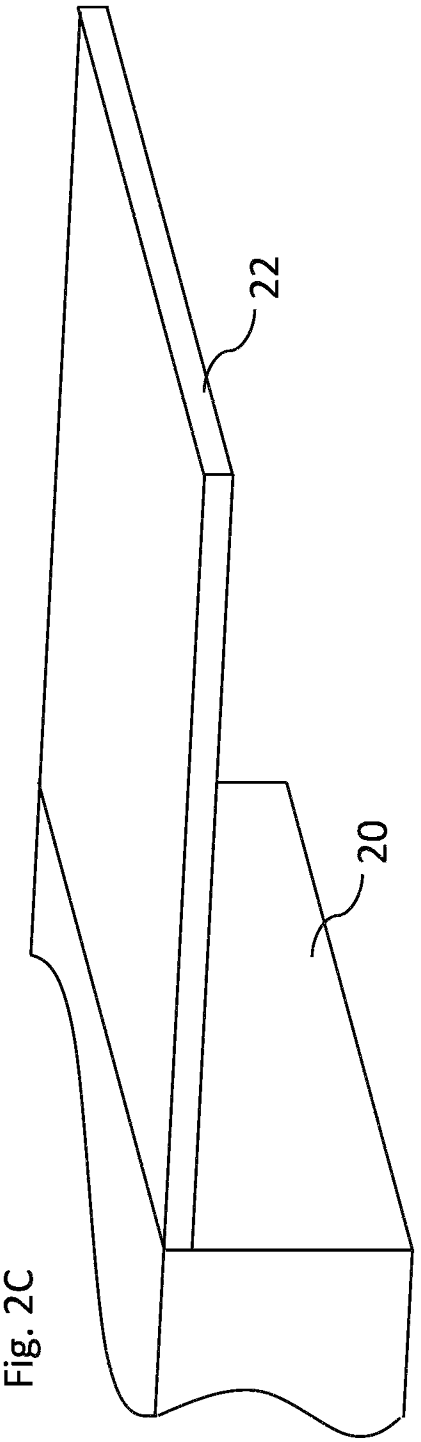
Figure 2D:
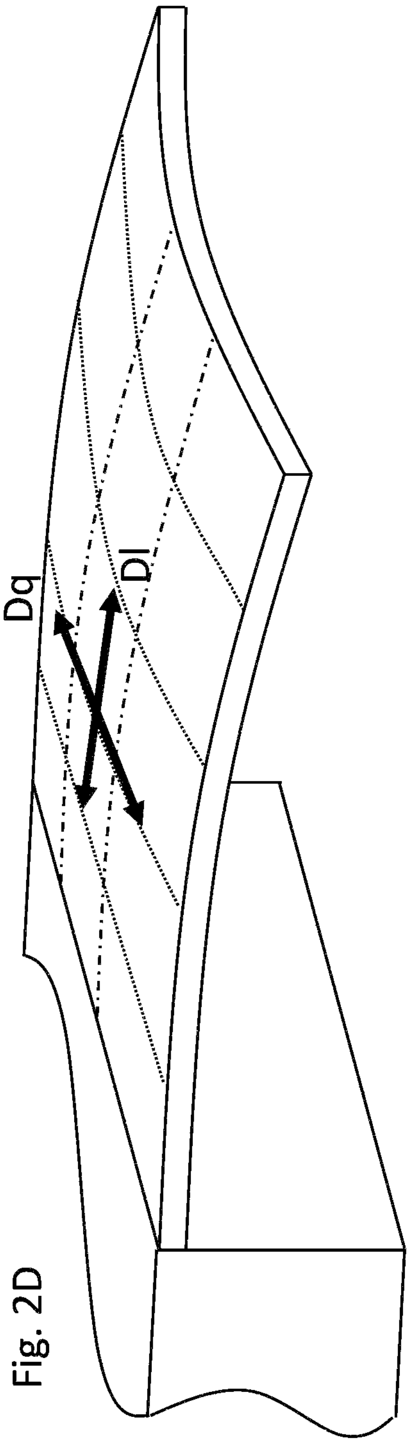

An important part is played in particular by the orientation of the transducers relative to the orientation of the cantilevers. FIG. 2C shows, for example, an undeflected cantilever. When the cantilever comes into contact with the analyte, there is a change in the surface stress and a deformation of the material, as shown in FIG. 2D. In FIG. 2D the cantilever undergoes a deformation perpendicularly to the base 20, or to the bending edge. This is accompanied by a longitudinal stretching DI of the upper surface. At the same time there is a deformation parallel to the base 20, or to the bending edge, which is accompanied by a transverse stretching Dq of the upper surface. With the geometry of the cantilever, it is possible to specify the direction along which a larger stretching D is brought about. The transducer may in particular be oriented along this direction in order to generate a particularly large measurement signal.

By the overdimensioning of a mechanical stretch at the location of the transducer, the signal emitted by the transducer may be improved still further. Such overdimensioning may be achieved, for example, through the arrangement and shape of the electrodes.

Figure 3A:
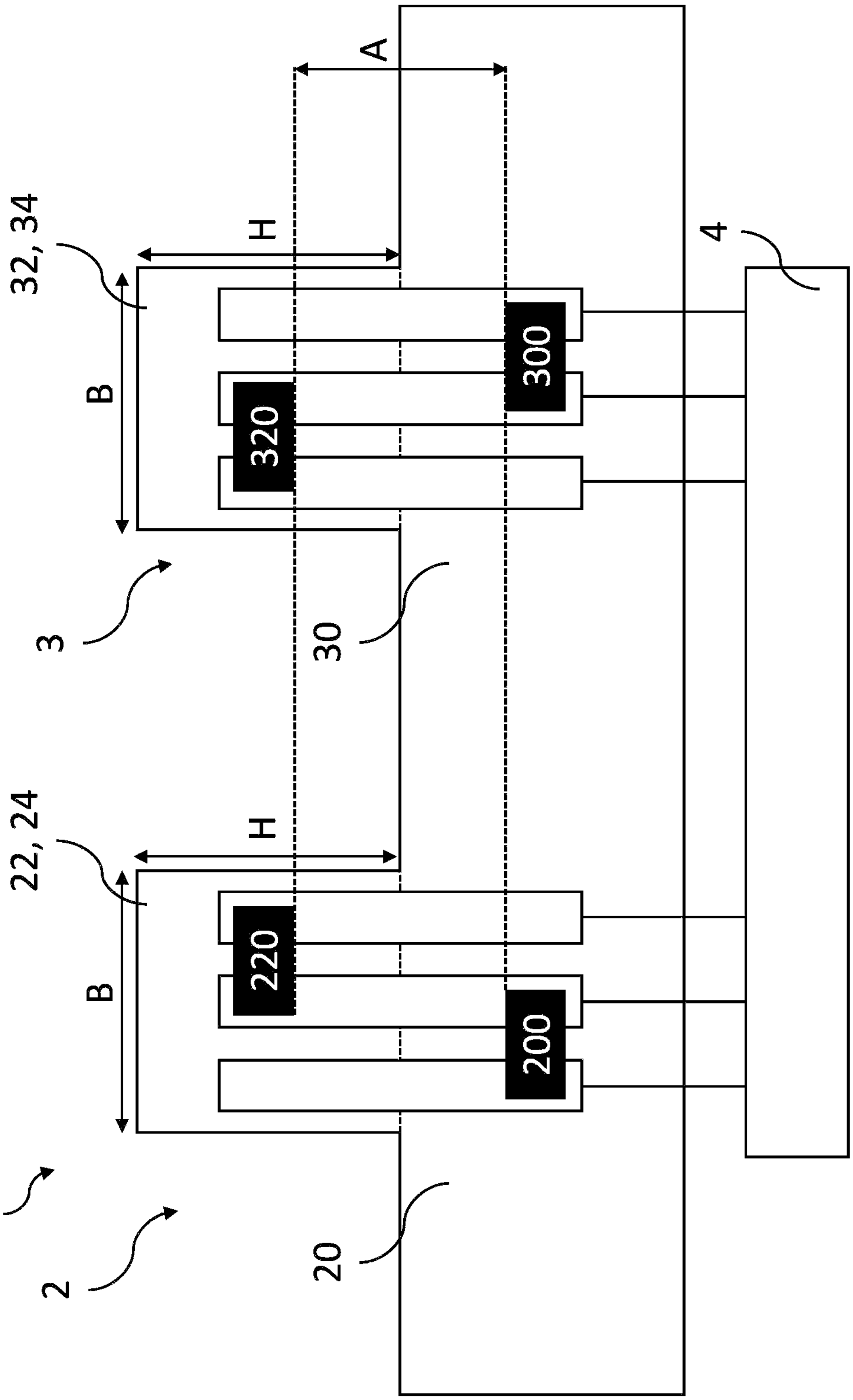
FIGS. 3A, B show a schematic representation of a second embodiment of the sensor.

FIG. 3A shows a further embodiment of the sensor 1. The reference cantilever 3 and the test cantilever 2 in particular have identical geometrical dimensions; more particularly, the height, width and thickness of the reference cantilever 3 correspond to the height, width and thickness of the test cantilever 2. This generates an equal stretching D on the upper surfaces 260, 360. As the geometrical dimensions of the cantilevers 2, 3 are identical, an identical dependency of the measurement signal on the stretching is also expected accordingly.

The width B of the cantilevers is preferably equal to the height H of the cantilevers 2, 3, thereby enabling a particularly large stretching D on the upper surface 260, 360 of the cantilever 2, 3. In this case, for example, the cantilevers are less than 100 μm wide, less than 100 μm long and less than 1 μm thick, more particularly 50 μm wide, 50 μm long and 0.3 μm thick.

In the embodiments of the sensor 1 in FIG. 3, the bases 30, 20 of the reference and test cantilevers 3, 2 are also arranged on the same overall base. Accordingly, there is a direct mechanical connection and interaction of the cantilevers via the overall base. This makes it possible for example to reduce the various ambient influences on the cantilevers 2, 3, since the cantilevers 2, 3 can be arranged closer to one another. In particular the bases 30, 20 of the reference and test cantilevers 3, 2 may also be formed in one piece. This ensures that the bases as well have identical material-specific binding properties, and so the measurement outcomes from the passive and active transducers 200, 300, 220, 320 are readily comparable with one another.

The distance A between the active transducers 320, 220 and the passive transducers 300, 200 is measured along the height direction H of the cantilevers. The distance A is in particular less than 100 μm, which ensures that the transducers are arranged very close to one another, so that, for example spatial ambient influences on the transducers are reduced.

Figure 3B:
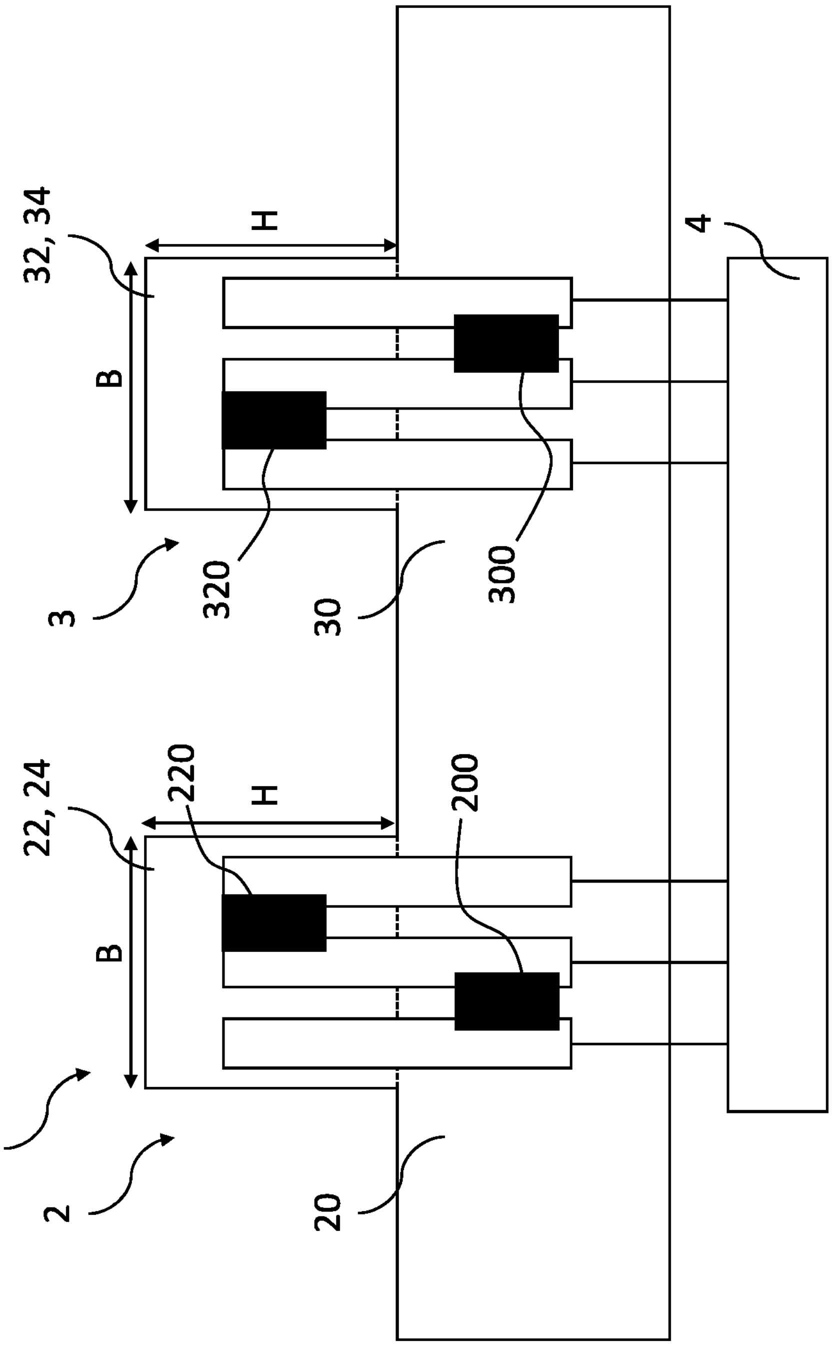

FIG. 3B shows a further embodiment in which the transducers 200, 220, 300 and 320 are oriented perpendicularly to the base 20, 30. Where with the transverse orientation of the transducer along the bending edge in FIG. 3A a transverse stretching of the cantilevers 22, 32 is measured, a longitudinal stretching of the cantilevers 22, 32 is measured in FIG. 3B.

Figure 4:
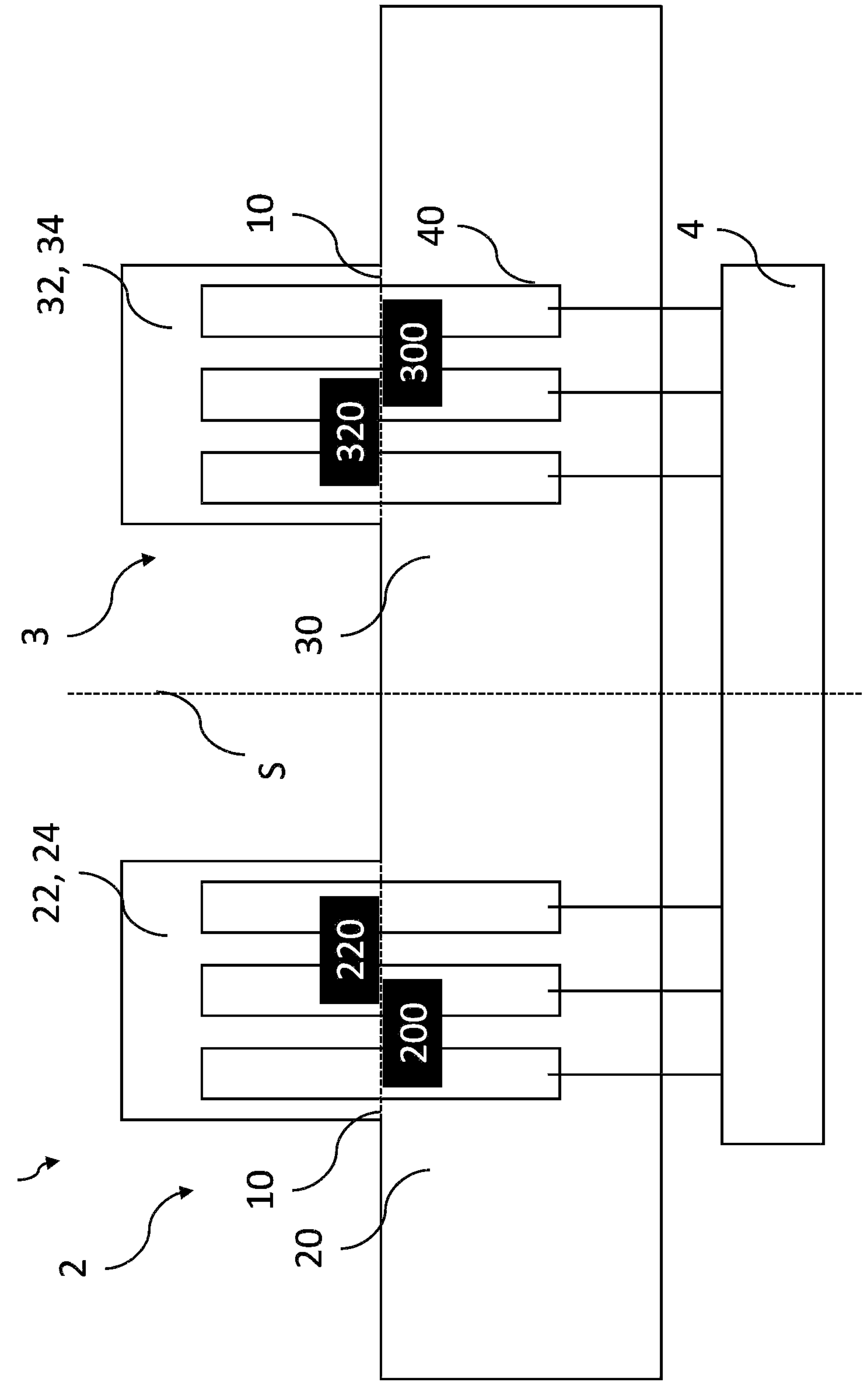
FIG. 4 shows a schematic representation of a third embodiment of the sensor.

FIG. 4 shows a preferred embodiment in this regard, in which the active transducers 320, 220 and the passive transducers 300, 200 lie in each case against the bending edge 10 of the cantilevers 3, 2. With all of the transducers 320, 300, 220, 200 lying against the bending edge 10, the minimum possible distance A between the transducers 320, 300, 220, 200 is realized. Furthermore, in this embodiment, the electrodes 40 and also the transducers 320, 300, 220, 200 are oriented mirror-symmetrically to an axis S of mirror symmetry. In particular the transducers 320, 300, 220, 200 are therefore oriented mirror-symmetrically to one another.

Figure 5A:
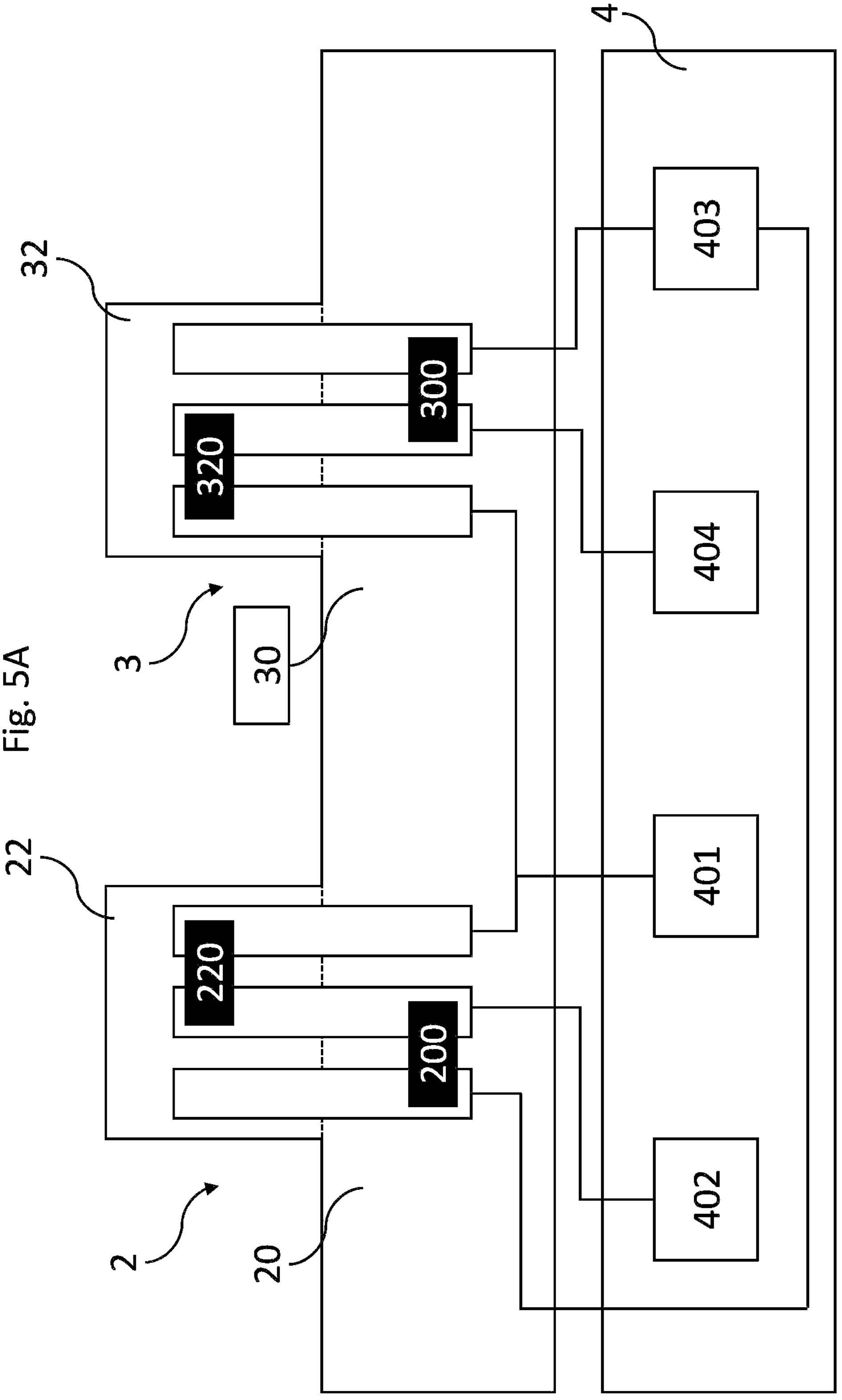
FIGS. 5A, B, C show further schematic representations of further embodiments of the sensor, and a circuit diagram of a full bridge.

FIG. 5A shows a further embodiment of the sensor 1. The transducers 300, 320, 200, 220 are contacted via the electrodes 401, 402, 403, 404. In particular the active transducer 220 is connected to the active transducer 320 via the electrode 401. Moreover, the passive transducer 200 is connected to the passive transducer 300 via the electrode 403. The active transducer 220, moreover, is connected to the passive transducer 200 via the electrode 402, whereas the active transducer 320 is connected to the passive transducer 300 via the electrode 404. All in all, therefore, there are four electrodes via which the transducers are electrically contacted with one another. Electrical contacting in this case may be achieved more particularly by applying the transducers to the electrodes, to produce a conductive connection. Since the transducers have a thickness, it may in particular be the case that, on subsequent application of electrodes, no conductive contacting to the electrodes would be achieved at the edges of the transducers. This is ensured only if the thickness of the electrodes is greater than the thickness of the transducers.

Figure 5B:
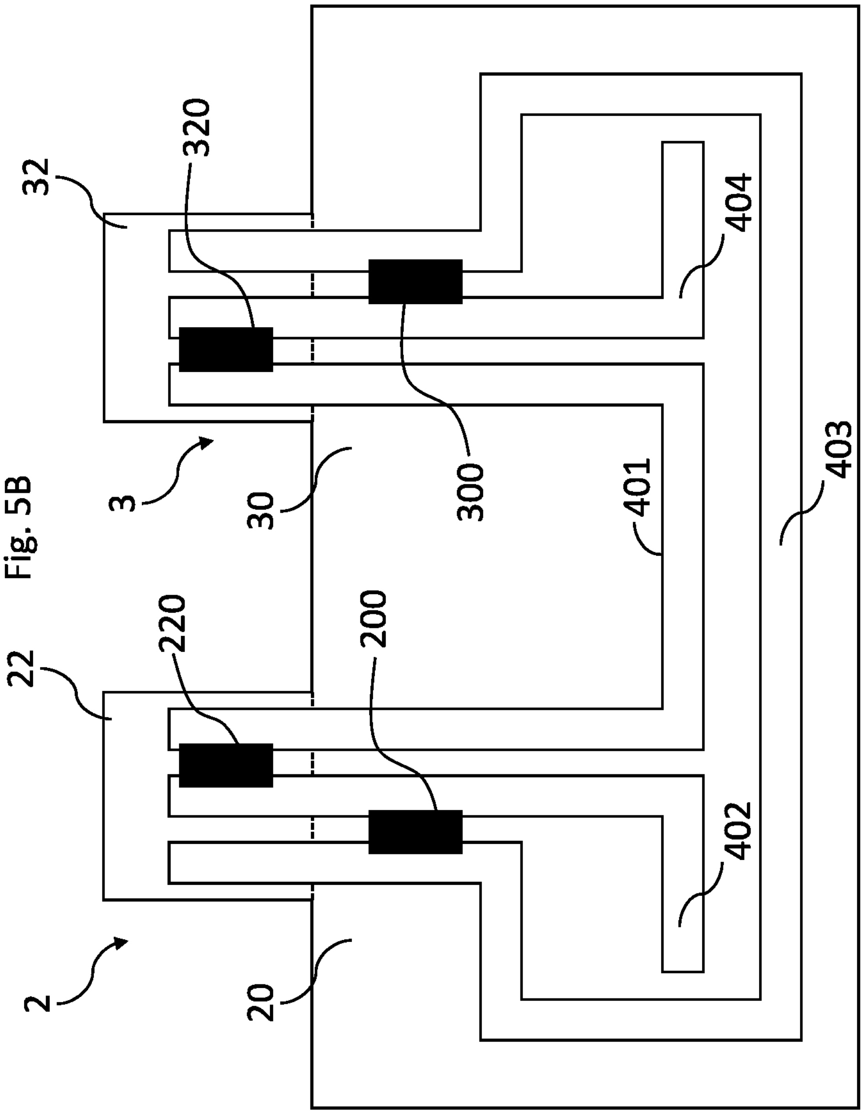

FIG. 5B shows a further embodiment of the sensor 1. The electrodes contacting the transducers 200, 220, 300, 320 have a mirror-symmetrical construction overall. Currents run through the electrodes or voltages are present there, and so, with an asymmetrical design of these electrodes, there may be asymmetrical crosstalk of electrical signals with the other electrodes. This mutual influencing may result in the generation of a control signal between the electrodes, but this may be avoided through the symmetrical construction.

Figure 5C:
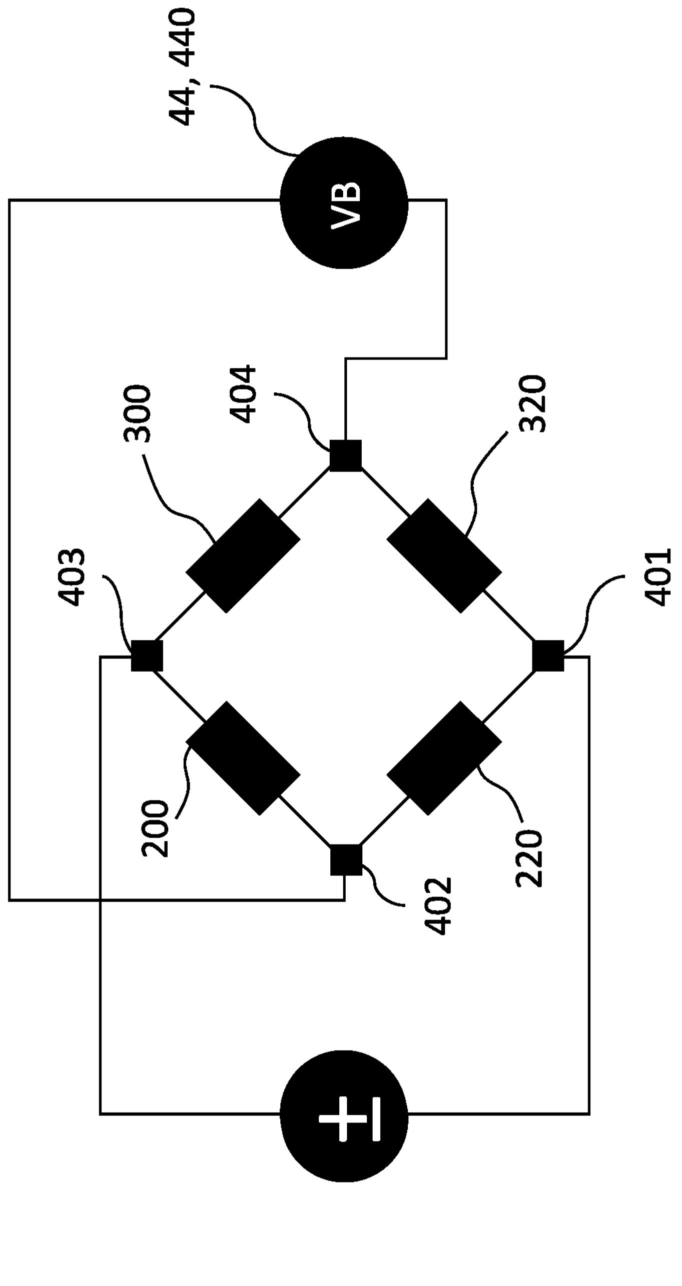

The transducers 200, 220, 300, 320 are interconnected electrically in particular in what is called a full bridge. The circuit of the full bridge is shown in FIG. 5C. With the full bridge, a DC voltage or AC voltage is applied between the electrodes 403, 401. The passive and active transducers act as voltage dividers between these electrodes, on the basis of their electrical resistances. A full bridge in the form shown has the advantage that no voltage is developed between the electrodes 402, 404 provided the ratio of the resistances of the passive transducer 200 to the active transducer 220 of the test cantilever 2 is equal to the ratio of the resistances of the passive transducer 300 to the active transducer 320 of the reference cantilever 3. All that is needed in order to change the resistance ratios, therefore, is the deviation of one resistance in particular, which is also sufficient to develop a voltage between the electrodes 402, 404 in this way.

If the reference cantilever 3 and the test cantilever 2 interact with the sample 9 and the analyte 90, then both deformable parts 22, 32 experience, for example, a change in surface stress, which is greater for the deformable part 22 of the test cantilever 2 than for the deformable part 32 of the reference cantilever 3. Accordingly, the resistance of the active test transducer of the deformable part 22 of the test cantilever 2 will vary to a greater extent than for the active reference transducer 320 of the deformable part 32 of the reference cantilever 3. If the resistances of the passive transducers 200, 300 do not change or at least change equally, there is a change in the resistance ratios arising from the deformation of the deformable part 22 of the test cantilever 2 because of the interaction with the analyte 90 of the sample 9, which interacts specifically with the reference layer 24 of the test cantilever 2. In the event of such interaction, accordingly, a voltage is developed between the electrodes 402, 404, and so a force acting on the active test transducer 220 relative to the active reference transducer 320 may be indicated as a transverse bridge voltage VB. The transverse bridge voltage VB preferably scales with the incidence of the analyte 90 in the sample 9, thereby enabling a quantitative evaluation of the measurement signal.

A transverse bridge voltage detector 44 is able to indicate the transverse bridge voltage VB externally or transmit it, allowing the user of the sensor 1 to see that there is a transverse bridge voltage VB present. In particular, a transverse bridge voltage detector 44 of this kind may also be formed by A/D converter, with the A/D converter converting the transverse bridge voltage VB into a digital signal which can be transmitted to the external measuring apparatus. The A/D converter may be operated in particular in two different measuring modes. The first measuring mode is the differential measuring mode, in which the transverse bridge voltage VB is measured and therefore a relative measurement value for the deformation of the two reference and test cantilevers 3, 2 is generated. In this differential measuring mode, so to speak, the measurement signals of all the transducers 200, 220, 300, 320 are taken into consideration, and so the output signal from the A/D converter is a measurement signal with ambient influences removed, and can be used to derive the relative deformation of the deformable parts 22, 32 and therefore the incidence of an analyte 90.

The second measuring mode is what is called the absolute measuring mode. In the absolute measuring mode, the transverse bridge voltage is not detected, but instead the signals at the electrodes 402 and 404 respectively are tapped off in isolation from one another, and so it is possible to make a statement regarding the respective deflections of the deformable parts 32, 22. This information remains unavailable to the user in the differential measuring mode.

Figure 6:
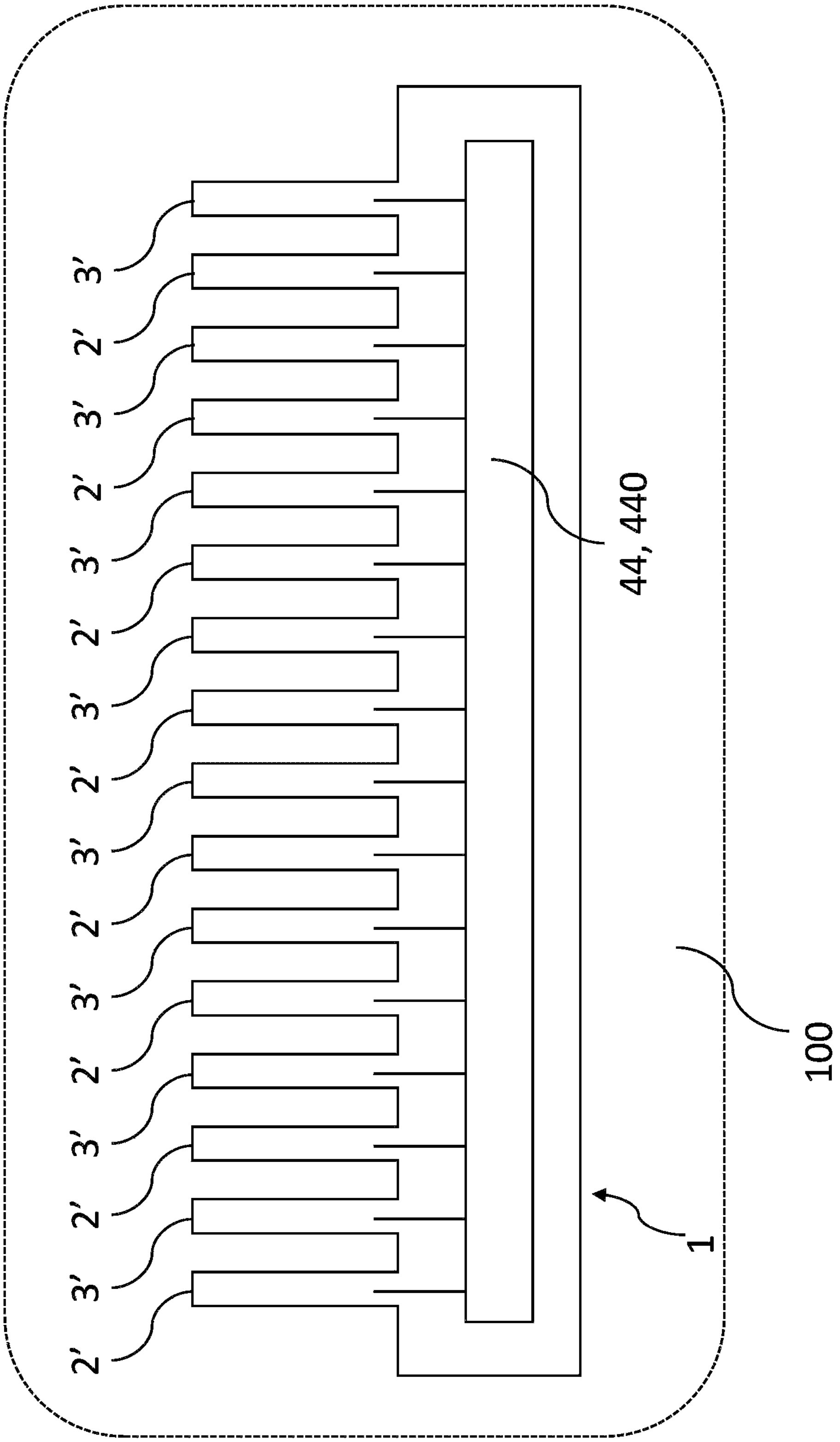
FIG. 6 shows a schematic representation of a chip having multiple cantilever pairs.

FIG. 6 shows a further embodiment of the sensor 1. The sensor 1 in this case comprises multiple cantilever pairs, with each cantilever pair here comprising a reference cantilever 3' and a test cantilever 2'. The reference cantilever 3' and test cantilever 2', or the corresponding transducers, are electrically connected to one another via an electrode circuit, as in FIGS. 5A to C, and consequently it is possible to tap off a transverse bridge voltage VB' for each cantilever pair. The transverse bridge voltage VW can be tapped off from each cantilever pair by the A/D converter 440, or by the transverse bridge voltage detector 44. In particular in the A/D converter 440, via an A/D converter logic unit, for example, it is possible to output the measurement signal from one particular cantilever pair or to output the integrated measurement signals from all the cantilever pairs, or a combination thereof. It is therefore possible in particular to average the measurement signals over different cantilever pairs, meaning that an incidence of an analyte 90 is indicated with greater statistical significance. It is, however, also possible for different reference layers and receptor layers 34, 24 to be applied on the various cantilever pairs, and so a sensor 1 of this kind enables the sample 9 to be investigated simultaneously for different analytes 90. It is also possible, however, for example, for a single reference cantilever 3 to serve as reference for multiple test cantilevers 2.

In particular, the sensor 1 may be embodied with the multiplicity of cantilever pairs on a chip 100. A chip here may mean that the sensor 1 has been fabricated from a single substrate, and so, for example, the various cantilevers 2, 3 are mechanically connected to one another. It may also be the case, however, that the chip 100 comprises a further electronic circuit, which is, for example, a CMOS circuit, i.e., a semiconductor circuit that taps off the transverse bridge voltage VB and processes it further directly. A semiconductor circuit of this kind in combination with a sensor is also called a system-on-a-chip.

Figure 7:
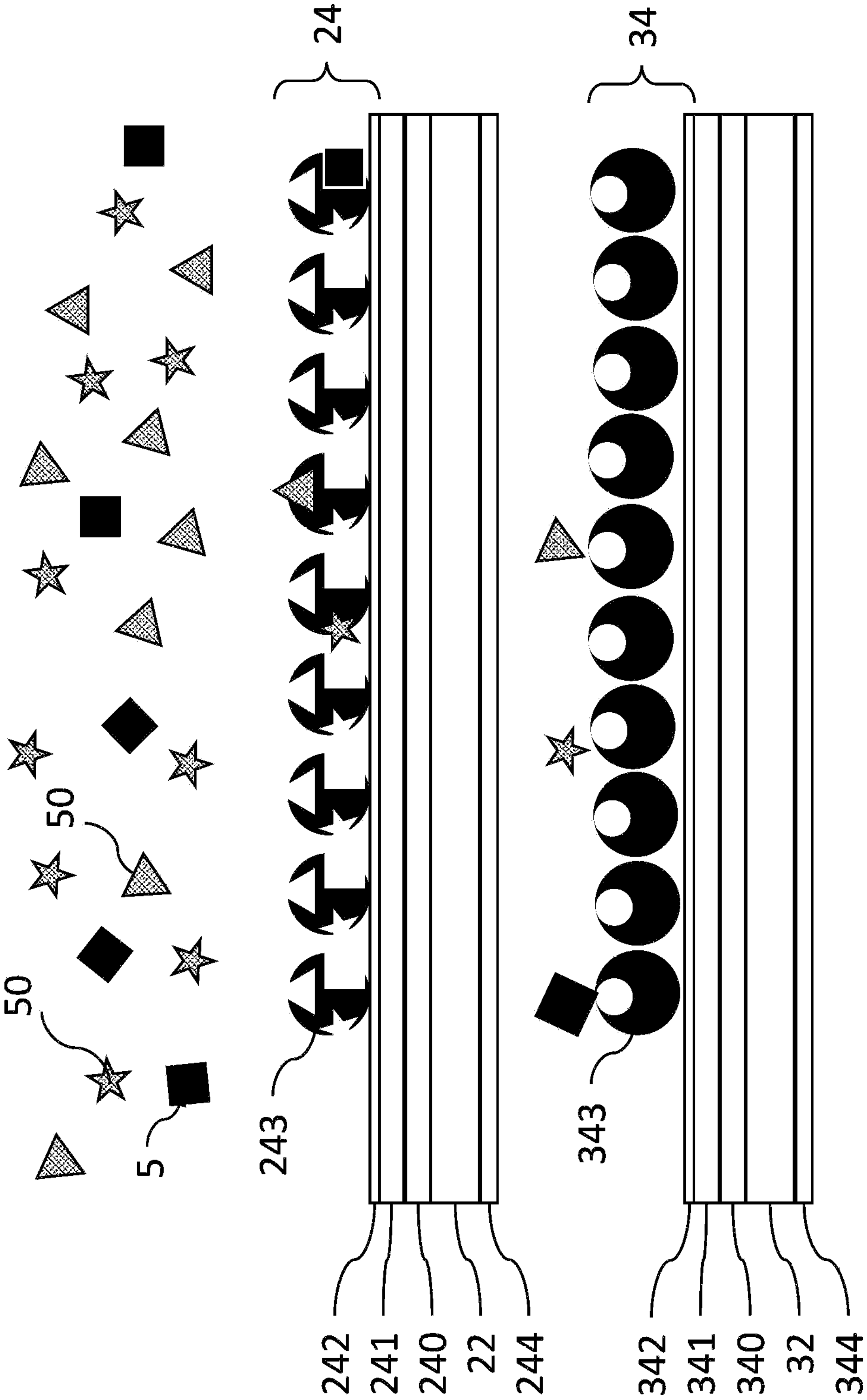
FIG. 7 shows a schematic representation of the binding of antigens to antibodies.

FIG. 7 shows schematically the construction of the various deformable parts 22, 32 of the reference and test cantilevers 3, 2, respectively. The construction of the cantilevers is identical except for the receptor layer and the reference layer, respectively, and so interaction with the sample or with the surrounding medium, and also the mechanical design of the cantilever, are very mostly identical.

On the deformable parts 32, 22 of the reference and test cantilevers 3, 2, respectively, an activation layer 34, 24 is applied. An activation layer 240 is configured to promote adhesion between the surface of the deformable part 32, 22 and a further layer 241, 341. The activation layer 240, furthermore, has the function of producing an asymmetrical layer construction of the cantilever 3, 2, so that there is as large as possible a difference in the stretching of the upper surface of the cantilever and the lower surface of the cantilever. The adhesion promoter layer, or the activation layer 240, may in particular comprise gold or consist of gold.

Atop the gold layer 240 there may then be a so called self-assembling monolayer 241 applied, which is able to compensate the surface unevennesses of the gold layer and which at the same time provides adhesion promotion for a further layer, specifically the reference and receptor layers 34, 24.

The construction of the reference layer and the receptor layer 34 and 24, respectively, is different. Both layers, however, are based on a layer which may comprise the so-called protein A 242, which firstly binds to the self-assembling monolayer 241, 341 but also has and is able to bind antibodies 243 or isotype control antibodies 343 on its surface.

The antibodies 243 are proteins which respond to an antigen 5, or bind to it, and which therefore, in the human immune system, label virus cells, allowing the immune system to destroy the labeled virus accordingly, in order for example to stem or to prevent a viral outbreak. The antibodies 243 are mostly specific to the antigen 5, but may also interact with other, similar antigens 50. FIG. 7 shows that the antibody 243 is able to interact to some extent with the antigen 5 and with the similar antigens 50.

In contrast to the antibody 243, the isotype control antibody 343 is a protein which preferably does not interact in an ultra-highly specific manner with the antigen 5. As a result, interaction with a specific antigen 5 can be virtually ruled out. This is shown in FIG. 7 by the fact that the isotype control antibody 343 is able to interact only with two similar antigens 50, but not with the antigen 5, shown schematically in square form here. As a result, the relative change in the surface stress of the cantilevers 22, 32 is attributable solely to the specific antigen 5.

As the test cantilever 2 has an antibody 243 and the reference cantilever 3 has an isotype control antibody 343, it is ensured that in the sample 9, the analyte 90, where the analyte 90 is an antigen 5, is able to interact only with the test cantilever 2. This ensures that the relative deformation of the test cantilever 2 brought about by the analyte, in comparison with the deformation of the reference cantilever 3, is based only on the presence of the analyte 90, or of the antigen 5. Accordingly, with this sensor 1 it is possible to detect an antigen 5 quickly and reliably. In contrast to the upper surface of the cantilevers, the lower surface of the cantilevers is passivated. Such passivation may lead to any interaction, or binding, or absorption or absorption of an analyte 90 from the sample 9 is avoided in or on the cantilever. In particular, however, a passivation layer of this kind also contributes to increasing the asymmetry of the layer construction, in order to maximize the stretching effect at the upper surface of the cantilever 3, 2. The passivation layer may in particular comprise trimethoxysilane and/or a blocking substance.

The sensor shown may be used in particular to detect the antigens 5 of a Sars-CoV2 virus or of another virus. For this purpose, the receptor layer 24 of the test cantilever 2 comprises, for example, Sars-CoV2 antibodies, whereas the reference layer 34 comprises Sars-CoV2-specific isotype control antibodies. A measurement signal is generated accordingly by the sensor 1 if the antigens 5 of a Sars-CoV2 virus are present in the sample 9 and accumulate at the test cantilever 2 or the receptor layer 24.

Insofar as is applicable, all individual features represented in the embodiments may be exchanged and/or combined with one another without departing from the scope of the invention.

LIST OF REFERENCE SIGNS

1 sensor
10 bending edge
2 test cantilever
20 base
200 passive test transducer
22 deformable part
220 active test transducer
24 receptor layer
240 activation layer
241 self-assembling monolayer
242 protein A
243 antibody
244 passivation layer
26 surface
260 upper surface
262 lower surface
3 reference cantilever
30 base
300 passive reference transducer
32 deformable part
320 active reference transducer
34 reference layer
340 activation layer
341 self-assembling monolayer
342 protein A
343 isotype control antibody
344 passivation layer
36 surface
360 upper surface
362 lower surface
4 electronic unit
40 electrode
400, 401, 402, 403 electrodes
42 transverse bridge voltage detector
44 AD converter
440 AD converter logic unit
5 antigen
50 similar antigen
9 sample
90 analyte
F force
L deflection
D stretching
AT distance between active and passive transducer
AE distance between electrodes
S axis of symmetry
VB transverse bridge voltage

What is claimed:

1. A sensor for converting at least one of chemical and biochemical information about an analyte in a sample into an electrical signal, the sensor comprising a test cantilever having a base and a deformable part on which a receptor layer for selective reception of the analyte is applied, where a passive test transducer is arranged on the base and an active test transducer is arranged on the deformable part;

a reference cantilever having a base and a deformable part on which a reference layer for selective non-reception of the analyte is applied, where a passive reference transducer is arranged on the base and an active reference transducer is arranged on the deformable part, wherein the active and passive reference transducers and the active and passive test transducers are configured to output an electrical signal corresponding to at least one of an incidence, a concentration and an amount of the analyte in the sample, wherein the sensor comprises electrodes configured to electrically contact the transducers, wherein the transducers are electrically interconnected in a full bridge that is configured to develop a transverse bridge voltage (VB) based on the electrical properties of the transducers, wherein an even number of electrodes is used, wherein a base signal level arising at the electrodes due to potential differences is less than 1.1V, and wherein the electrodes are free from electrical encapsulation.

2. The sensor according to claim 1, wherein the transducers are each configured to determine an alteration in a surface stress of the reference cantilever and of the test cantilever.

3. The sensor according to claim 1, wherein the transducers are each configured to determine at least one of a deformation and an alteration in a surface stress of the respective deformable parts of the reference cantilever and of the test cantilever, and wherein the changes in at least one of the surface stress and a force (F) exerted during deformation on each respective base and the deformable parts the reference cantilever and of the test cantilever are detected.

4. The sensor according to claim 3, wherein the force (F) to be detected is at least one of a bending force, a stretching force, a shearing force and a surface stress, or is due to an elasticity modulus of the reference and test cantilevers.

5. The sensor according to claim 3, wherein an effect on the test cantilever caused by the selective reception of the analyte is concluded through a comparison of the deformations, forces and/or surface stresses detected by the transducers.

6. The sensor according to claim 1, wherein the deformable parts of the reference and test cantilevers have identical geometric dimensions, and respective widths of the deformable part of the reference and test cantilevers corresponds to respective lengths of the deformable part of the reference and test cantilevers.

7. The sensor according to claim 1, wherein the respective bases of each of the reference and test cantilevers are arranged as a single base.

8. The sensor according to claim 1, wherein the reference and test cantilevers comprise at least one of Si3N4, SiO2, Si3N4/SiO2, SiC, Si or comprise a polymer.

9. The sensor according to claim 1, wherein the transducers have identical intrinsic physical properties and are configured to adapt electrical properties in accordance with forces acting on the reference and test cantilevers.

10. The sensor according to claim 1, wherein a distance (A) between each respective active transducer and each corresponding passive transducer on a same cantilever is less than 100 μm.

11. The sensor according to claim 1, further comprising a transverse bridge voltage detector that is configured to detect the transverse bridge voltage (VB) of the full bridge, wherein an incidence of the analyte selectively received by the receptor layer is concluded through the detected transverse bridge voltage (VB).

12. The sensor according to claim 1, wherein electrical properties of the transducers are output via an A/D converter, and an A/D converter logic unit is configured to provide at least one of a differential measurement and an absolute measurement of bending states.

13. The sensor according to claim 12, wherein the sensor is embodied on a chip and a multiplicity of cantilever pairs are arranged on the chip, wherein each cantilever pair comprises a test cantilever and a reference cantilever, wherein the A/D converter logic unit is configured to provide signal multiplexing of the measurement signals.

14. The sensor according to claim 1, further comprising:

an activation layer configured to activate upper surfaces of the reference and test cantilevers, wherein the activation layer is configured to provide a greater surface stress in comparison to a non-activated lower surface of the reference and test cantilevers, and wherein the activation layer comprises gold.

15. The sensor according to claim 1, further comprising:

a passivation layer that passivates lower surfaces of the reference and test cantilevers, wherein the passivation layer is configured to minimize an unspecific protein adhesion on the reference and test cantilevers, and wherein the passivation layer comprises at least one of trimethoxysilane and a blocking substance.

16. The sensor according to claim 1, wherein the reference and test cantilevers each comprise a self-assembling monolayer.

17. The sensor according to claim 1, wherein the receptor layer comprises antibodies for an antigen, and the reference layer comprises an antigen-specific isotype control antibody according to the antibody of the reference layer.

18. The sensor according to claim 1, wherein:

the receptor layer provides molecule-specific binding forces and the reference layer provides no binding forces molecule-specifically, or the receptor layer comprises single-strand DNA (ssDNA) and/or other DNA fragments which binds specifically to DNA fragments in the sample, and the reference layer comprises single-strand DNA and/or other DNA fragments which does not bind to any chemical and/or biochemical and/or physical species in the sample but in characteristic parameters coincides with the receptor layer, or the receptor layer comprises single-strand RNA and/or other RNA fragments which binds specifically to RNA fragments in the sample, and the reference layer comprises single-strand RNA and/or other RNA fragments which does not bind to any chemical and/or biochemical and/or physical species in the sample but in characteristic parameters coincides with the receptor layer, or the receptor layer comprises antibodies and/or other and/or further proteins which are able to specifically bind target proteins, and the reference layer comprises specific isotype control antibodies and/or other and/or further proteins which do not bind to any chemical and/or biochemical and/or physical species in the sample, or the receptor layer comprises scFv antibodies and the reference layer comprises scFV antibody-specific isotype control antibodies; or the receptor layer comprises Sars-CoV2 antibodies and the reference layer comprises Sars-CoV2 specific isotype control antibodies; or the receptor layer and the reference layer comprise hydrogels.

19. The sensor according to claim 2, wherein at least one of the deformation and the alteration in the surface stress is achieved in a transverse direction of at least one of the test cantilever and the reference cantilever, wherein the transverse direction runs parallel to the base of at least one of the test cantilever and the reference cantilever.

20. The sensor according to claim 2, wherein at least one of the deformation and the alteration in the surface stress is achieved in a longitudinal direction of at least one of the test cantilever and the reference cantilever, where the longitudinal direction runs perpendicular to the base of at least one of the test cantilever and of the reference cantilever.

* * * * *